(12) United States Patent
McCuen

(10) Patent No.: US 8,967,443 B2
(45) Date of Patent: Mar. 3, 2015

(54) METHOD AND APPARATUS FOR DETERMINING PARAMETERS OF LINEAR MOTION IN A SURGICAL INSTRUMENT

(75) Inventor: David M. McCuen, Straford, CT (US)

(73) Assignee: Covidien LP, Mansfield, MA (US)

( * ) Notice: Subject to any disclaimer, the term of this patent is extended or adjusted under 35 U.S.C. 154(b) by 1029 days.

(21) Appl. No.: 13/033,622

(22) Filed: Feb. 24, 2011

(65) Prior Publication Data

US 2011/0139851 A1    Jun. 16, 2011

Related U.S. Application Data

(63) Continuation-in-part of application No. 12/189,834, filed on Aug. 12, 2008.

(60) Provisional application No. 61/314,189, filed on Mar. 16, 2010, provisional application No. 60/997,854, filed on Oct. 5, 2007.

(51) Int. Cl.
*A61B 17/068* (2006.01)
*A61B 17/072* (2006.01)
(Continued)

(52) U.S. Cl.
CPC . *A61B 17/07207* (2013.01); *A61B 2017/00017* (2013.01); *A61B 2017/00022* (2013.01); *A61B 2017/00199* (2013.01); *A61B 2017/00367* (2013.01); *A61B 2017/00734* (2013.01); *A61B 2019/2292* (2013.01); *A61B 2019/467* (2013.01); *A61B 2019/4857* (2013.01)
USPC .................................... 227/175.1; 227/182.1

(58) Field of Classification Search
CPC ..................... A61B 17/007207; A61B 17/072; A61B 2017/068

USPC ............................................ 227/175.1, 182.1
See application file for complete search history.

(56) References Cited

U.S. PATENT DOCUMENTS

| 4,331,277 A | 5/1982 | Green |
| 4,606,343 A | 8/1986 | Conta et al. |

(Continued)

FOREIGN PATENT DOCUMENTS

| EP | 1 728 475 A2 | 12/2006 |
| EP | 1 813 203 A | 8/2007 |

(Continued)

OTHER PUBLICATIONS

Extended European Search from European Application No. 10250228.3 mailed on Jun. 1, 2010.

(Continued)

*Primary Examiner* — Gloria R Weeks

(57) ABSTRACT

A surgical instrument and method of controlling the surgical instrument are disclosed. The surgical instrument includes a housing and an elongated shaft that extends distally from the housing and defines a first longitudinal axis. The surgical instrument also includes a firing rod disposed in the elongated shaft and a drive mechanism disposed at least partially within the housing. The drive mechanism mechanically cooperates with the firing rod to move the firing rod. A sensor senses a parameter of light reflected from the surface of the firing rod, which includes markings that change the reflectivity of the firing rod. The measurement unit determines a parameter of the motion of the firing rod, such as the position and speed of the firing rod, based on the sensed parameter of the light reflected from the surface of the firing rod.

15 Claims, 20 Drawing Sheets

(51) Int. Cl.
  *A61B 17/00* (2006.01)
  *A61B 19/00* (2006.01)

(56) References Cited

U.S. PATENT DOCUMENTS

| | | | |
|---|---|---|---|
| 4,705,038 A | 11/1987 | Sjostrom et al. | |
| 4,807,628 A | 2/1989 | Peters et al. | |
| 5,129,570 A | 7/1992 | Schulze et al. | |
| 5,143,453 A | 9/1992 | Weynant nee Girones | |
| RE34,519 E | 1/1994 | Fox et al. | |
| 5,312,023 A | 5/1994 | Green et al. | |
| 5,313,935 A | 5/1994 | Kortenbach et al. | |
| 5,326,013 A | 7/1994 | Green et al. | |
| 5,350,355 A | 9/1994 | Sklar | |
| 5,359,993 A | 11/1994 | Slater et al. | |
| 5,383,874 A | 1/1995 | Jackson et al. | |
| 5,383,880 A | 1/1995 | Hooven | |
| 5,389,098 A | 2/1995 | Tsuruta et al. | |
| 5,395,033 A | 3/1995 | Byrne et al. | |
| 5,400,267 A | 3/1995 | Denen et al. | |
| 5,413,267 A | 5/1995 | Solyntjes et al. | |
| 5,467,911 A | 11/1995 | Tsuruta et al. | |
| 5,487,499 A | 1/1996 | Sorrentino et al. | |
| 5,518,163 A | 5/1996 | Hooven | |
| 5,518,164 A | 5/1996 | Hooven | |
| 5,529,235 A | 6/1996 | Boiarski et al. | |
| 5,535,934 A | 7/1996 | Boiarski et al. | |
| 5,535,937 A | 7/1996 | Boiarski et al. | |
| 5,562,239 A | 10/1996 | Boiarski et al. | |
| 5,609,560 A | 3/1997 | Ichikawa et al. | |
| 5,653,374 A | 8/1997 | Young et al. | |
| 5,667,517 A | 9/1997 | Hooven | |
| 5,704,534 A | 1/1998 | Huitema et al. | |
| 5,713,505 A | 2/1998 | Huitema | |
| 5,779,130 A | 7/1998 | Alesi et al. | |
| 5,782,397 A | 7/1998 | Koukline | |
| 5,823,066 A | 10/1998 | Huitema et al. | |
| 5,830,121 A | 11/1998 | Enomoto et al. | |
| 5,954,259 A | 9/1999 | Viola et al. | |
| 5,991,355 A | 11/1999 | Dahlke | |
| 5,992,724 A | 11/1999 | Snyder | |
| 6,017,354 A | 1/2000 | Culp et al. | |
| 6,063,095 A | 5/2000 | Wang et al. | |
| 6,090,123 A | 7/2000 | Culp et al. | |
| 6,165,169 A | 12/2000 | Panescu et al. | |
| 6,166,538 A | 12/2000 | D'Alfonso | |
| 6,236,874 B1 | 5/2001 | Devlin et al. | |
| 6,237,604 B1 | 5/2001 | Burnside et al. | |
| 6,295,330 B1 | 9/2001 | Skog et al. | |
| 6,329,778 B1 | 12/2001 | Culp et al. | |
| 6,387,092 B1 | 5/2002 | Burnside et al. | |
| 6,388,240 B2 | 5/2002 | Schulz et al. | |
| 6,461,372 B1 | 10/2002 | Jensen et al. | |
| 6,515,273 B2 | 2/2003 | Al-Ali | |
| 6,533,157 B1 | 3/2003 | Whitman | |
| 6,578,579 B2 | 6/2003 | Burnside et al. | |
| 6,601,748 B1 | 8/2003 | Fung et al. | |
| 6,611,793 B1 | 8/2003 | Burnside et al. | |
| 6,651,669 B1 | 11/2003 | Burnside | |
| 6,699,177 B1 | 3/2004 | Wang et al. | |
| 6,716,233 B1 | 4/2004 | Whitman | |
| 6,736,085 B1 | 5/2004 | Esnouf | |
| 6,792,390 B1 | 9/2004 | Burnside et al. | |
| 6,793,652 B1 | 9/2004 | Whitman et al. | |
| 6,846,307 B2 | 1/2005 | Whitman et al. | |
| 6,846,308 B2 | 1/2005 | Whitman et al. | |
| 6,846,309 B2 | 1/2005 | Whitman et al. | |
| 6,849,071 B2 | 2/2005 | Whitman et al. | |
| 6,861,639 B2 | 3/2005 | Al-Ali | |
| 6,899,538 B2 | 5/2005 | Matoba | |
| 6,959,852 B2 | 11/2005 | Shelton, IV et al. | |
| 6,981,628 B2 | 1/2006 | Wales | |
| 6,981,941 B2 | 1/2006 | Whitman et al. | |
| 7,032,798 B2 | 4/2006 | Whitman et al. | |
| 7,048,687 B1 | 5/2006 | Reuss et al. | |
| 7,077,856 B2 | 7/2006 | Whitman | |
| 7,111,769 B2 | 9/2006 | Wales et al. | |
| 7,118,564 B2 | 10/2006 | Ritchie et al. | |
| 7,143,925 B2 | 12/2006 | Shelton, IV et al. | |
| 7,143,926 B2 | 12/2006 | Shelton, IV et al. | |
| 7,186,966 B2 | 3/2007 | Al-Ali | |
| 7,193,519 B2 | 3/2007 | Root et al. | |
| 7,217,269 B2 | 5/2007 | El-Galley et al. | |
| 7,220,232 B2 | 5/2007 | Suorsa et al. | |
| 7,240,817 B2 | 7/2007 | Higuchi | |
| 7,241,270 B2 | 7/2007 | Horzewski et al. | |
| 7,328,828 B2 | 2/2008 | Ortiz et al. | |
| 7,335,169 B2 | 2/2008 | Thompson et al. | |
| 7,364,061 B2 | 4/2008 | Swayze et al. | |
| 7,380,695 B2 | 6/2008 | Doll et al. | |
| 7,380,696 B2 | 6/2008 | Shelton, IV et al. | |
| 7,404,508 B2 | 7/2008 | Smith et al. | |
| 7,464,847 B2 * | 12/2008 | Viola et al. | 227/175.2 |
| 7,717,312 B2 | 5/2010 | Beetel | |
| 7,784,663 B2 | 8/2010 | Shelton, IV | |
| 7,954,682 B2 * | 6/2011 | Giordano et al. | 227/175.1 |
| 7,959,050 B2 * | 6/2011 | Smith et al. | 227/175.2 |
| 8,011,551 B2 * | 9/2011 | Marczyk et al. | 227/175.1 |
| 8,028,882 B2 * | 10/2011 | Viola | 227/175.1 |
| 8,517,239 B2 * | 8/2013 | Scheib et al. | 227/175.1 |
| 2003/0073981 A1 | 4/2003 | Whitman et al. | |
| 2004/0094597 A1 | 5/2004 | Whitman et al. | |
| 2004/0232199 A1 | 11/2004 | Shelton, IV et al. | |
| 2005/0006429 A1 | 1/2005 | Wales et al. | |
| 2005/0006430 A1 | 1/2005 | Wales | |
| 2005/0006431 A1 | 1/2005 | Shelton, IV et al. | |
| 2005/0006434 A1 | 1/2005 | Wales et al. | |
| 2005/0023324 A1 | 2/2005 | Doll et al. | |
| 2005/0139636 A1 | 6/2005 | Schwemberger et al. | |
| 2005/0187576 A1 | 8/2005 | Whitman et al. | |
| 2005/0247753 A1 | 11/2005 | Kelly et al. | |
| 2006/0000867 A1 | 1/2006 | Shelton, IV et al. | |
| 2006/0022014 A1 | 2/2006 | Shelton, IV et al. | |
| 2006/0022015 A1 | 2/2006 | Shelton, IV et al. | |
| 2006/0212069 A1 | 9/2006 | Shelton, IV | |
| 2006/0278680 A1 | 12/2006 | Viola et al. | |
| 2007/0005002 A1 | 1/2007 | Millman et al. | |
| 2007/0016174 A1 | 1/2007 | Millman et al. | |
| 2007/0023476 A1 | 2/2007 | Whitman et al. | |
| 2007/0023477 A1 | 2/2007 | Whitman et al. | |
| 2007/0029363 A1 | 2/2007 | Popov | |
| 2007/0029364 A1 | 2/2007 | Kruszynski et al. | |
| 2007/0039995 A1 | 2/2007 | Schwemberger et al. | |
| 2007/0039996 A1 | 2/2007 | Mather et al. | |
| 2007/0039997 A1 | 2/2007 | Mather et al. | |
| 2007/0084896 A1 | 4/2007 | Doll et al. | |
| 2007/0084897 A1 | 4/2007 | Shelton, IV et al. | |
| 2007/0102472 A1 | 5/2007 | Shelton, IV | |
| 2007/0102473 A1 | 5/2007 | Shelton, IV et al. | |
| 2007/0102474 A1 | 5/2007 | Shelton, IV et al. | |
| 2007/0102475 A1 | 5/2007 | Ortiz et al. | |
| 2007/0125826 A1 | 6/2007 | Shelton, IV | |
| 2007/0152014 A1 | 7/2007 | Gillum et al. | |
| 2007/0156121 A1 | 7/2007 | Millman et al. | |
| 2007/0158385 A1 | 7/2007 | Hueil et al. | |
| 2007/0167960 A1 | 7/2007 | Roth et al. | |
| 2007/0175949 A1 | 8/2007 | Shelton, IV et al. | |
| 2007/0175950 A1 | 8/2007 | Shelton, IV et al. | |
| 2007/0175951 A1 | 8/2007 | Shelton, IV et al. | |
| 2007/0175952 A1 | 8/2007 | Shelton, IV et al. | |
| 2007/0175953 A1 | 8/2007 | Shelton, IV et al. | |
| 2007/0175955 A1 | 8/2007 | Shelton, IV et al. | |
| 2007/0175956 A1 | 8/2007 | Swayze et al. | |
| 2007/0175957 A1 | 8/2007 | Shelton, IV et al. | |
| 2007/0175958 A1 | 8/2007 | Shelton, IV et al. | |
| 2007/0175959 A1 | 8/2007 | Shelton, IV et al. | |
| 2007/0175960 A1 | 8/2007 | Shelton, IV et al. | |
| 2007/0175961 A1 | 8/2007 | Shelton, IV et al. | |
| 2007/0175962 A1 | 8/2007 | Shelton, IV et al. | |
| 2007/0175964 A1 | 8/2007 | Shelton, IV et al. | |
| 2007/0187453 A1 | 8/2007 | Smith et al. | |
| 2007/0219563 A1 | 9/2007 | Voegele | |
| 2007/0278277 A1 | 12/2007 | Wixey et al. | |
| 2008/0029570 A1 | 2/2008 | Shelton et al. | |

(56) References Cited

U.S. PATENT DOCUMENTS

| | | |
|---|---|---|
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0046122 A1 | 2/2008 | Manzo et al. |
| 2008/0048002 A1 | 2/2008 | Smith et al. |
| 2008/0110957 A1 | 5/2008 | McBride et al. |
| 2008/0135600 A1 | 6/2008 | Hiranuma et al. |
| 2008/0164296 A1 | 7/2008 | Shelton et al. |
| 2008/0185419 A1 | 8/2008 | Smith et al. |
| 2008/0255607 A1 | 10/2008 | Zemlok |
| 2009/0018390 A1* | 1/2009 | Honda et al. ............ 600/106 |
| 2009/0088774 A1 | 4/2009 | Swarup et al. |
| 2009/0088775 A1 | 4/2009 | Swarup et al. |
| 2009/0099520 A1 | 4/2009 | Millman et al. |
| 2009/0101692 A1* | 4/2009 | Whitman et al. ........ 227/175.1 |
| 2009/0138019 A1 | 5/2009 | Wasielewski |
| 2010/0200637 A1 | 8/2010 | Beetel |
| 2010/0225209 A1 | 9/2010 | Goldberg et al. |
| 2010/0228249 A1 | 9/2010 | Mohr et al. |
| 2010/0228264 A1 | 9/2010 | Robinson et al. |
| 2011/0062211 A1* | 3/2011 | Ross et al. ............... 227/175.1 |

FOREIGN PATENT DOCUMENTS

| | | |
|---|---|---|
| EP | 1943958 A1 | 7/2008 |
| EP | 2 005 875 A1 | 12/2008 |
| EP | 2 014 218 A2 | 1/2009 |
| EP | 2 044 890 A1 | 4/2009 |
| WO | WO 00/72765 A1 | 12/2000 |

OTHER PUBLICATIONS

European Search Report for EP 08253184.9-2310 date of completion is Feb. 12, 2009 (3 pages).

European Search Report EP 11 25 0309 dated Jun. 21, 2011.

* cited by examiner

METHOD AND APPARATUS FOR DETERMINING PARAMETERS OF LINEAR MOTION IN A SURGICAL INSTRUMENT

CROSS-REFERENCE TO RELATED APPLICATIONS

This application claims the benefit of and priority to U.S. Provisional Patent Application Ser. No. 61/314,189, filed on Mar. 16, 2010, the entire contents of which are incorporated by reference herein. This application is also a Continuation-in-Part of U.S. patent application Ser. No. 12/189,834, filed on Aug. 12, 2008, which claims the benefit of, and priority to, U.S. Provisional Patent Application Ser. No. 60/997,854, filed on Oct. 5, 2007, the entire contents of which are incorporated by reference herein.

BACKGROUND

1. Technical Field

The present disclosure relates to a method and apparatus for manipulating body tissue or deploying surgical fasteners into body tissue, and, in particular, to a method and apparatus for determining parameters of the motion of a firing rod in a surgical instrument based on the change in light reflected from the surface of the firing rod.

2. Background of Related Art

Current surgical instruments typically require 10-60 pounds of manual hand force to clamp body tissue and deploy surgical fasteners in body tissue. Repeated use of these surgical instruments can cause fatigue in a surgeon's hand. Powered surgical instruments were developed to, among other reasons, reduce or eliminate this fatigue. These powered surgical instruments include gas-powered pneumatic staplers, which implant surgical fasteners into body tissue. Certain of these instruments include a pressurized gas supply coupled to a firing mechanism and a trigger mechanism. The trigger mechanism, when depressed, releases pressurized gas, which, in turn, applies force to the firing mechanism to deploy a surgical fastener into body tissue.

Powered surgical instruments also include motor-powered surgical instruments. These surgical instruments include powered surgical staplers with motors that activate staple firing mechanisms. Typically, the motors are rotary motors mechanically coupled to a lead screw so that the motor can cause the lead screw to rotate. The lead screw has a continuous helical thread machined on its outer surface along its length (similar to the thread on a bolt). Threaded onto the lead screw is a nut with corresponding helical threads. The nut, however, does not rotate with the lead screw. In this configuration, when the lead screw is rotated by the motor, the nut is driven in a linear direction. The nut, in turn, drives a mechanism for manipulating body tissue or deploying a surgical fastener into body tissue. Alternatively, the lead screw is replaced by a firing rod with helical threads on its outside surface and the nut is replaced by a drive tube with corresponding threads on its inside surface (as described below). In this configuration, the motor rotates the drive tube and the drive tube, in turn, drives the firing rod in a linear direction. The firing rod, in turn, drives the mechanism for manipulating body tissue or deploying a surgical fastener into body tissue.

In some surgical instruments, a controller controls the motion of the firing mechanism (e.g., the nut or the firing rod) based on feedback from sensors that sense parameters of the linear motion of the firing mechanism (e.g., velocity). A conventional method of sensing parameters associated with the motion of a firing rod is to use a rotational sensor mechanically coupled to the rotary motor or the drive tube that drives the firing rod.

A typical rotational sensor includes an encoder wheel coupled to the drive shaft of the rotary motor (or the drive tube), a light generator, and an optical reader (e.g., photo interrupter). The encoder wheel includes a plurality of slits disposed around its outer edge and rotates with the drive shaft. The outer edge of the encoder wheel is disposed between the light generator and the optical reader so that the light generator emits a light beam through the slits to the optical reader. In other words, the light beam is interrupted by the encoder wheel as the drive shaft rotates. The optical reader determines the number of interruptions in the light beam and rate of interruptions and transmits these measurements to a processor, which determines the speed of the drive shaft. The processor then uses the speed of the drive shaft to calculate the linear velocity of the actuator (e.g., firing rod) mechanically coupled to the drive shaft.

Rotational sensors as well as other existing types of sensors, however, contribute in a significant way to the size, length, diameter, weight, and complexity of a surgical instrument. In addition, many of these sensors increase mechanical wear within the surgical instrument because the sensors mechanically interact with or repeatedly make physical contact with components of the surgical instrument. Therefore, there is a continual need for surgical instruments having sensors that reduce mechanical wear (for increased reliability), that reduce the complexity of the design of the surgical instrument (for reduced fabrication costs), and that reduce the size, length, diameter, and weight of the surgical instrument (for increased maneuverability during laparoscopic and endoscopic procedures).

SUMMARY

The present disclosure, in one aspect, features a surgical instrument. The surgical instrument includes a housing, an elongated shaft, a firing rod, a drive mechanism, a motion sensor, and a measurement unit. The elongated shaft extends distally from the housing and defines a first longitudinal axis. The firing rod is disposed within the elongated shaft and the drive mechanism is disposed at least partially within the housing. The drive mechanism mechanically cooperates with the firing rod. The motion sensor senses a parameter of light (e.g., visible light) reflected from the surface of the firing rod. The measurement unit determines a parameter of the motion of the firing rod based on a sensed change in the parameter of the light reflected from the surface of the firing rod. This sensor design does not mechanically interact with the firing rod and thus reduces the mechanical wear of the components of the surgical instrument. In addition, this sensor design is simple and minimizes the size of the surgical instrument for optimum maneuverability during surgical procedures.

In some embodiments, the motion sensor includes a light emitter and detector unit that generates and emits light on the surface of the firing rod and senses the parameter of the light reflected from the surface of the firing rod. In some embodiments, the light emitter and detector unit generates a pulse signal with a parameter that varies with the change in the parameters of the light reflected from the surface of the firing rod. In addition, the measurement unit determines the parameter of the motion of the firing rod based on the change in the parameter of the pulse signal. In some embodiments, the parameter of the pulse signal is the frequency of the pulse signal or the pulse width of the pulse signal.

In some embodiments, the measurement unit includes a counter that counts pulses in the pulse signal. In these embodiments, the measurement unit also includes a data processor that computes a pulse signal. In some embodiments, the surface of the firing rod includes a plurality of markings that vary the reflective properties of the surface of the firing rod. In these embodiments, the measurement unit includes a counter that counts the number of markings that are exposed to the light emitted from the light emitter and detector unit based on the sensed change in the parameter of the light reflected from the surface off the firing rod. In some embodiments, the measurement unit determines the parameter of the motion of the firing rod based on the pulse signal frequency.

In other embodiments, the parameter of the motion of the firing rod is the position or velocity of the firing rod and the parameter of the light is phase, frequency, intensity, or polarization. In yet other embodiments, the surgical instrument further includes a control unit that controls the drive mechanism based on the measured parameter of the motion of the firing rod determined by the measurement unit.

The present disclosure, in another aspect, features a method of determining a parameter of the motion of a firing rod in a surgical instrument. The method includes emitting light on the surface of a firing rod in a surgical instrument, sensing a change in a parameter of the light reflected from the surface of the firing rod, and determining a parameter of the motion of the firing rod based on the sensed change in the parameter of the light reflected from the surface of the firing rod.

The present disclosure, in yet another aspect, features a method of operating a surgical instrument. This method includes emitting light on the surface of a firing rod in a surgical instrument, sensing a change in a parameter of the light reflected from the surface of the firing rod, determining a parameter of the motion of the firing rod based on the sensed change in the parameter of the light reflected from the surface of the firing rod, and controlling the motion of the firing rod based on the determined parameter of the motion of the firing rod.

In some embodiments, sensing a change in a parameter of the light reflected from the surface of the firing rod includes generating a pulse signal with a parameter that varies with the change in the parameter of the light reflected from the surface of the firing rod, and determining the parameter of the motion of the firing rod includes determining the parameter of the motion of the firing rod based on the change in the parameter of the pulse signal. In other embodiments, sensing a change in the parameter of the light reflected from the surface of the firing rod includes counting the number of markings on the firing rod that are exposed to the light.

In some embodiments, the parameters of the motion of the firing rod include the position or velocity of the firing rod and the parameter of the light is phase, frequency, intensity, or polarization.

BRIEF DESCRIPTION OF THE DRAWINGS

Various embodiments of the subject instrument are described herein with reference to the drawings wherein.

DETAILED DESCRIPTION

Figure 1:
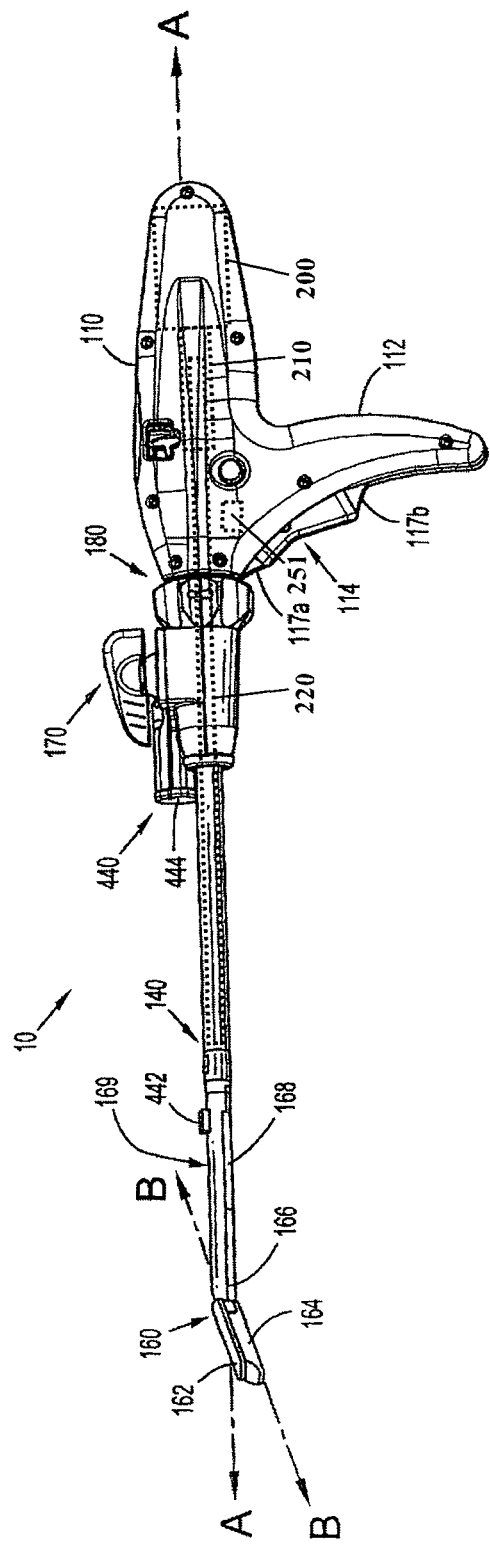
FIG. 1 is a perspective view of a surgical instrument including a motion sensor that includes a light emitter and detector unit in accordance with an embodiment of the present disclosure.

Embodiments of the presently disclosed surgical instrument are now described in detail with reference to the drawings, in which like reference numerals designate identical or corresponding elements in each of the several views. As used herein the term "distal" refers to that portion of the surgical instrument, or component thereof, farther from the user while the term "proximal" refers to that portion of the surgical instrument or component thereof, closer to the user.

A surgical instrument (e.g., a powered surgical stapler) in accordance with the present disclosure is referred to in the figures as reference numeral 10. Referring initially to FIG. 1, powered surgical instrument 10 includes a housing 110, an elongated shaft 140 defining a first longitudinal axis A-A, and an end effector 160 that defines a second longitudinal axis B-B. The elongated shaft 140 extends distally from the housing 110 and the end effector 160 is disposed adjacent a distal portion of the elongated shaft 140. In some embodiments, the elongated shaft 140 is configured for minimally invasive surgical procedures.

The housing 110 contains a drive motor 200, a drive tube 210, and a firing rod 220, and a motion sensor 251 (shown by the dotted lines). The drive motor 200 may be a rotary motor that drives the drive tube 210 in a radial direction. As described in more detail below, the drive tube 210 includes threads on its inner surface that correspond to threads on the outer surface of the firing rod 220 so that rotation of the drive tube 210 causes the firing rod 220 to move in a linear direction. The firing rod 220, in turn, actuates the end effector 160.

In certain surgical procedures, the firing rod 220 and the end effector 160 must be precisely controlled. According to embodiments of the present disclosure, the motion of the firing rod 220 is precisely controlled based on the actual motion of the firing rod 220 that is sensed by the motion sensor 251 (which includes a light emitter and detector unit described below). The motion sensor 251 senses actual motion of the firing rod 220 by emitting light on the surface of the firing rod 220 and detecting a parameter of the light reflected from the surface of the firing rod 220.

According to an embodiment of the present disclosure, end effector 160 includes a first jaw member having one or more surgical fasteners (e.g., cartridge assembly 164) and a second opposing jaw member including an anvil portion for forming the surgical fasteners (e.g., an anvil assembly 162). In some embodiments, staples are housed in cartridge assembly 164 to apply rows of staples to body tissue either in simultaneous or sequential manner. Either one or both of the anvil assembly 162 and the cartridge assembly 164 are movable in relation to one another between an open position in which the anvil assembly 162 is spaced apart from cartridge assembly 164 and an approximated or clamped position in which the anvil assembly 162 is in juxtaposed alignment with cartridge assembly 164. In other embodiments, the end effector 160 may be configured to deploy any type of surgical component used to join body tissue including fasteners, clips, staples, coils, or sutures. In yet other embodiments, the end effector 160 may be configured to rotate, articulate, extend, retract, clamp or cut.

End effector 160 is pivotably attached to a mounting portion 166, which, in turn, is attached to a body portion 168. Body portion 168 may be integral with the elongated shaft 140 of the surgical instrument 10, or may be removably attached to the surgical instrument 10 to provide a replaceable, disposable loading unit (DLU) or single use loading unit (SULU) (e.g., loading unit 169). In certain embodiments, the reusable portion may be configured for sterilization and re-use in a subsequent surgical procedure.

The loading unit 169 may connect to the elongated shaft 140 through a bayonet connection. The loading unit 169 may include an articulation link that connects the end effector 160 to the firing rod 220 so that the end effector 160 is articulated as the firing rod 220 is translated in the distal-proximal direction along the first longitudinal axis A-A. Other components for connecting end effector 160 to the elongated shaft 140 to allow articulation may be used, such as a flexible tube or a tube including a plurality of pivotable members.

The loading unit 169 may incorporate or be configured to incorporate various end effectors, such as vessel sealing devices, linear stapling devices, circular stapling devices, cutters, etc. These end effectors may be coupled to the elongated shaft 140 of the powered surgical instrument 10. The loading unit 169 may include a linear stapling end effector that does not articulate. An intermediate flexible shaft may be included between a handle portion 112 and the loading unit 169. A flexible shaft may facilitate access to and/or within certain areas of the body.

Figure 2:
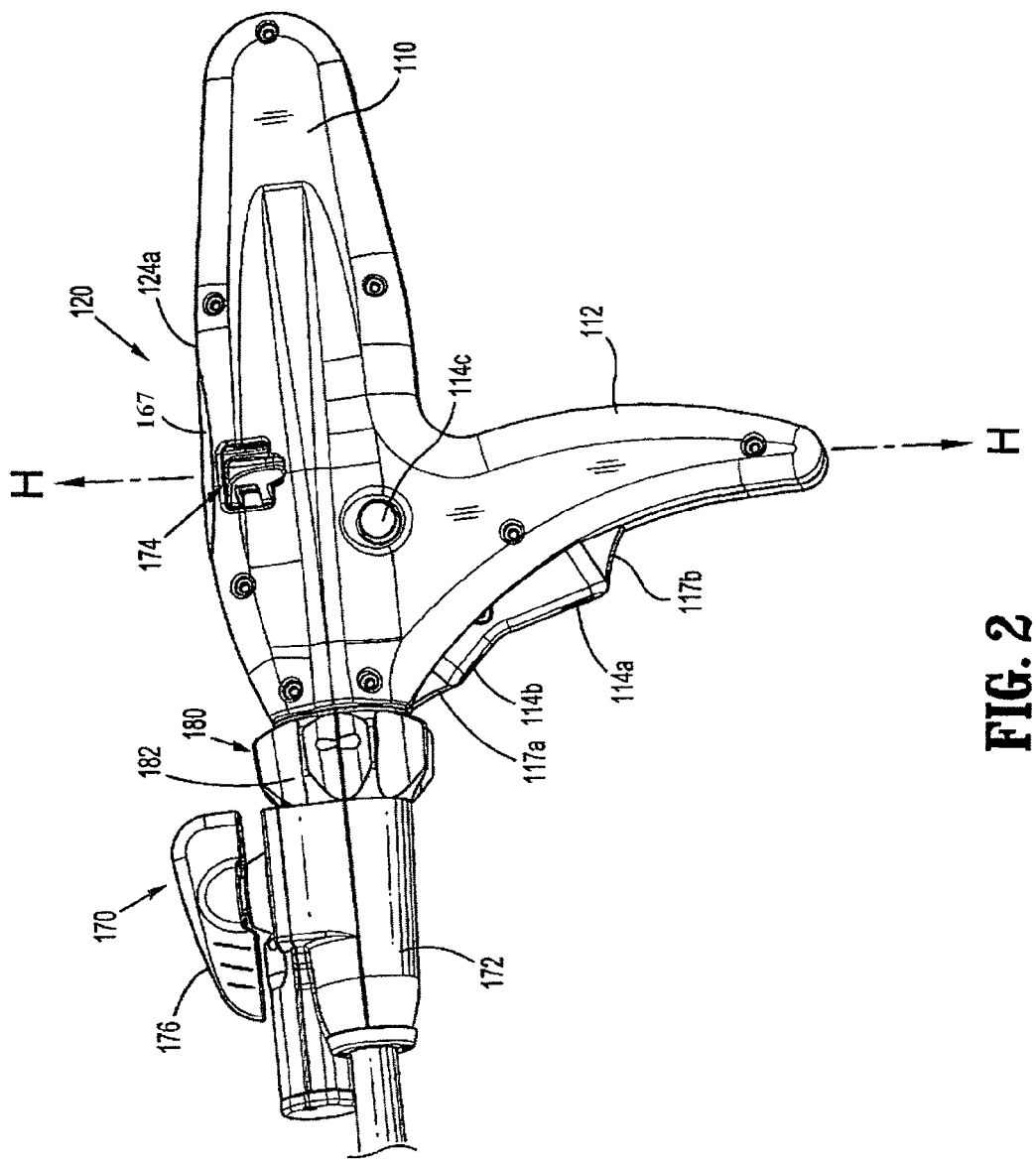
FIG. 2 is a partial perspective view of the powered surgical instrument of FIG. 1.

As shown in FIGS. 1 and 2, the housing 110 includes the handle portion 112 on which a main drive switch 114 is disposed. The switch 114 may include first and second switches 114a, 114b, which together form a toggle switch. The handle portion 112, which defines a handle axis H-H, is configured to be grasped by fingers of a user. The handle portion 112 has an ergonomic shape providing ample palm grip leverage, which helps keep the handle portion 112 from being squeezed out of the user's hand during operation. Each switch 114a, 114b is shown as being disposed at a suitable location on the handle portion 112 to facilitate its depression by a user's finger or fingers. In another embodiment, the surgical instrument 10 includes two separates switches 114a, 114b separated by a rib feature.

Figure 4:
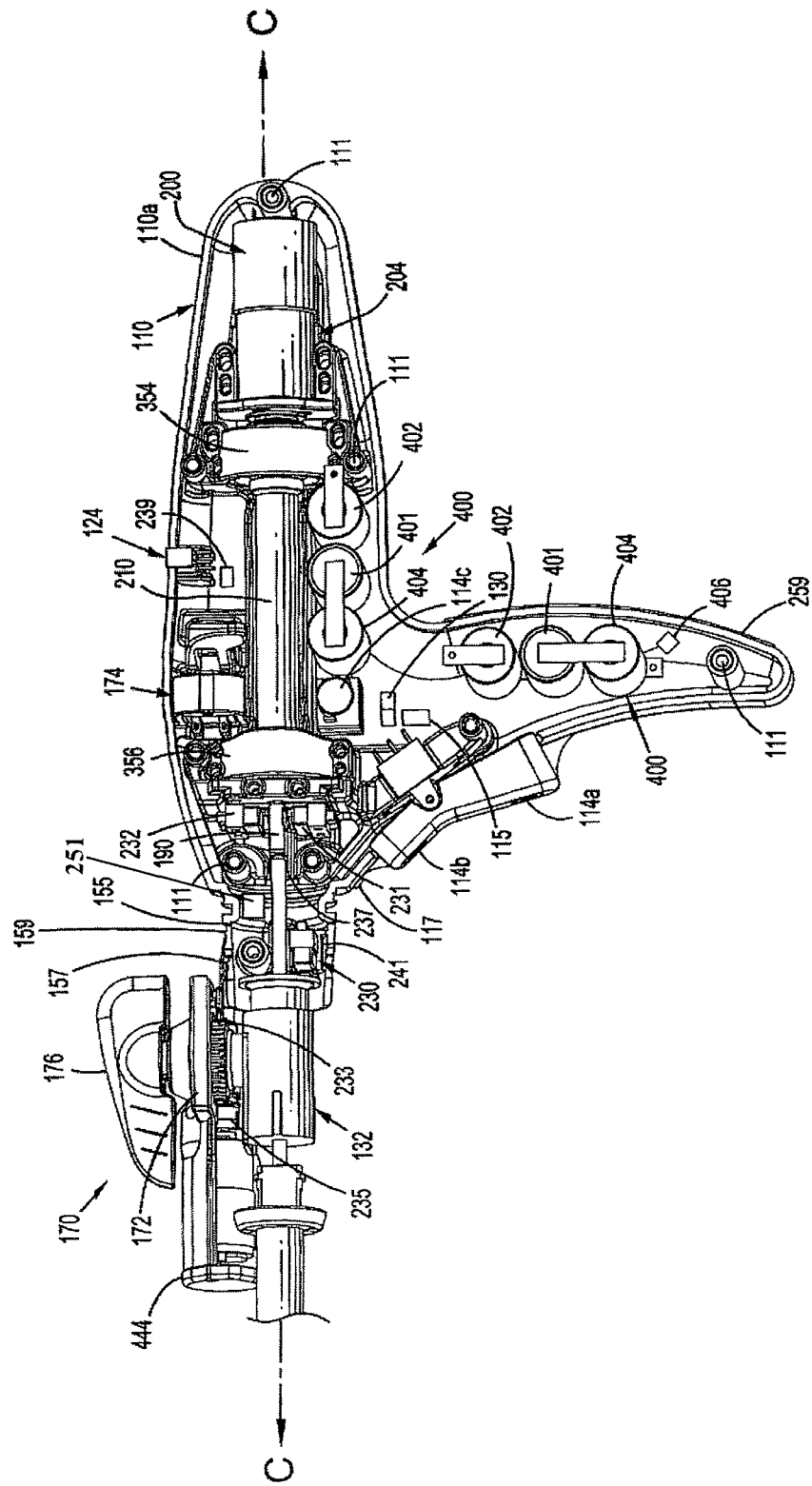
FIG. 4 is a perspective cut-away view of the powered surgical instrument of FIG. 2 in accordance with an embodiment of the present disclosure.
Figure 6:
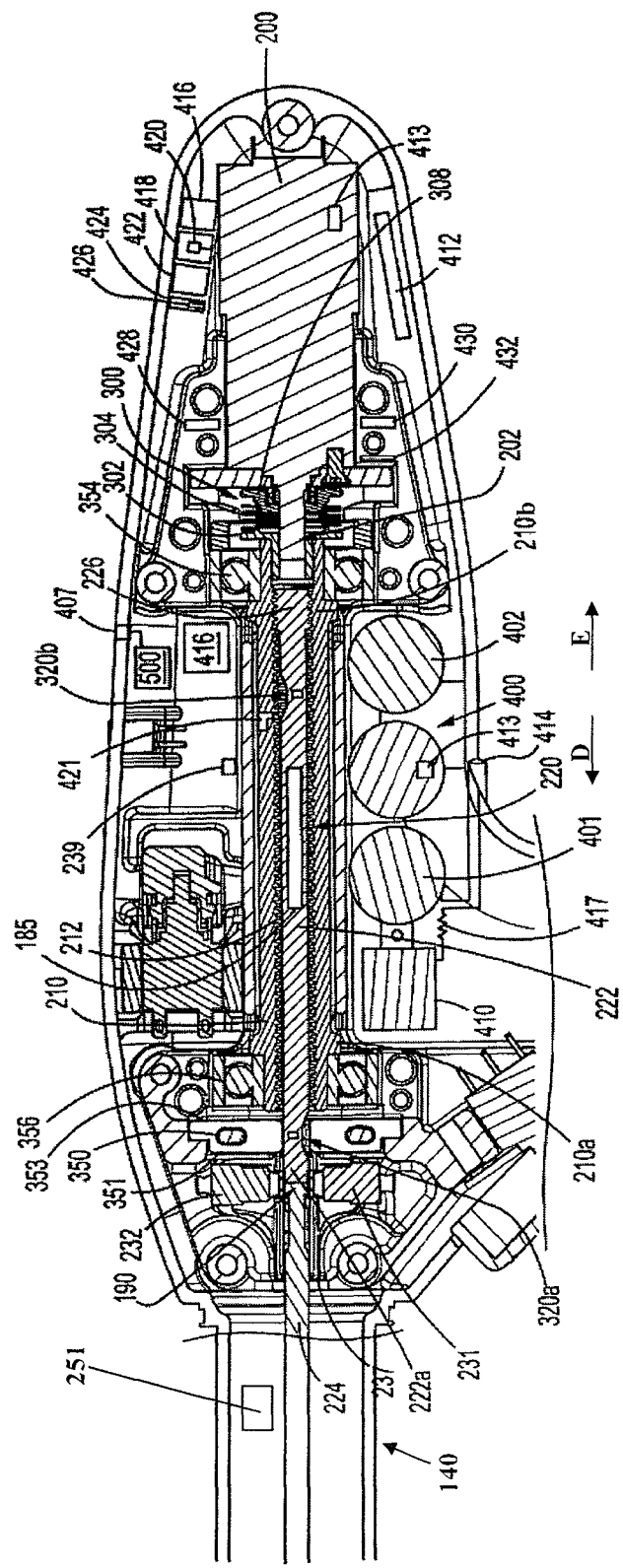
FIG. 6 is a partial cross-sectional view of the powered surgical instrument of FIG. 1.

Additionally, switches 114a, 114b may be used for starting and/or stopping movement of a drive motor 200 (FIGS. 1, 4 and 6). In one embodiment, the switch 114a is configured to activate the drive motor 200 in a first direction to advance firing rod 220 (FIGS. 1 and 6) in a distal direction thereby clamping the anvil and cartridge assemblies 162, 164. Conversely, the switch 114b may be configured to retract the firing rod 220 to open the anvil and cartridge assemblies 162, 164 by activating the drive motor 200 in a second direction opposite of the first direction. The retraction mode initiates a mechanical lock out, inhibiting further progression of stapling and cutting by the loading unit 169. The toggle has a first position for activating switch 114a, a second position for activating switch 114b, and a neutral position between the first and second positions.

The housing 110, in particular the handle portion 112, includes switch shields 117a, 117b. The switch shields 117a, 117b may have a rib-like shape surrounding the bottom portion of the switch 114a and the top portion of the switch 114b, respectively. The switch shields 117a, 117b minimize accidental activation of the switches 114a, 114b. Further, the switches 114a, 114b have high tactile feedback requiring increased pressure for activation.

In one embodiment, the switches 114a, 114b are configured as multi-speed (e.g., two or more speeds), incremental-speed or variable-speed switches that control the speed of the drive motor 200 and the firing rod 220 in a non-linear manner. For example, the switches 114a, 114b can be pressure-sensitive. This type of control interface allows for the gradual increase in the rate of the speed of the drive components from a slower and more precise mode to a faster operation. To minimize accidental activation of retraction, the switch 114b may be disconnected electronically until a fail-safe switch is pressed. In addition, a third switch 114c may also be used for this purpose. Additionally or alternatively, the fail safe can be overcome by pressing and holding the switch 114b for a predetermined period of time from about 100 ms to about 2 seconds. The firing rod 220 then automatically retracts to its initial position unless the switch 114c is activated (e.g., pressed and released) during the retraction mode to stop the retraction. Subsequent pressing of the switch 114b resumes the retraction of the firing rod 220. Alternatively, in other embodiments, the retraction of the firing rod 220 can continue to full retraction even if the switch 114b is released. Other embodiments include an auto-retract mode of the firing rod 220 that fully retracts the firing rod 220 even if switch 114b is released. The retraction mode may be interrupted at any time if one of the switches 114a, 114b is actuated.

The switches 114a, 114b are coupled to a non-linear speed control circuit 115 which can be implemented as a voltage regulation circuit, a variable resistance circuit, or a microelectronic pulse width modulation circuit. The switches 114a, 114b may interface with the control circuit 115 (FIG. 4) by displacing or actuating variable control devices, such as rheostatic devices, multiple position switch circuit, linear and/or rotary variable displacement transducers, linear and/or rotary potentiometers, optical encoders, ferromagnetic sensors, and Hall Effect sensors. This allows the switches 114a, 114b to operate the drive motor 200 in multiple speed modes, such as gradually increasing the speed of the drive motor 200 either incrementally or gradually depending on the type of the control circuit 115 being used, based on the depression of the switches 114a, 114b.

In a particular embodiment, the switch 114c may be actuated to mechanically and/or electrically change the mode of operation from clamping to firing. The switch 114c is recessed within the housing 110 and has high tactile feedback to inhibit false actuations. Providing a separate control switch to initialize the firing mode allows for the jaws of the end effector to be repeatedly opened and closed so that the surgical instrument 10 is used as a grasper until the switch 114c is pressed to activate the stapling and/or cutting. The switch 114 may include one or more microelectronic membrane switches. Such a microelectronic membrane switch includes a relatively low actuation force, a small package size, an ergonomic size and shape, a low profile, an ability to include molded letters on the switch, symbols, depictions and/or indications, and a low material cost. Additionally, the switches 114a, 114b (such as microelectronic membrane switches) may be sealed to help facilitate sterilization of the surgical instrument 10, as well as to help inhibit particle and/or fluid contamination.

As an alternative to, or in addition to the switches 114a, 114b, other input devices may include voice input technology, which may include hardware and/or software incorporated in a control system (not shown), or a separate digital module. The voice input technology may include voice recognition, voice activation, voice rectification and/or embedded speech. The user may control the operation of the instrument in whole or in part through voice commands, thus freeing one or both of the user's hands for operating other instruments. Voice or other audible output may also be used to provide the user with feedback.

Figure 3:
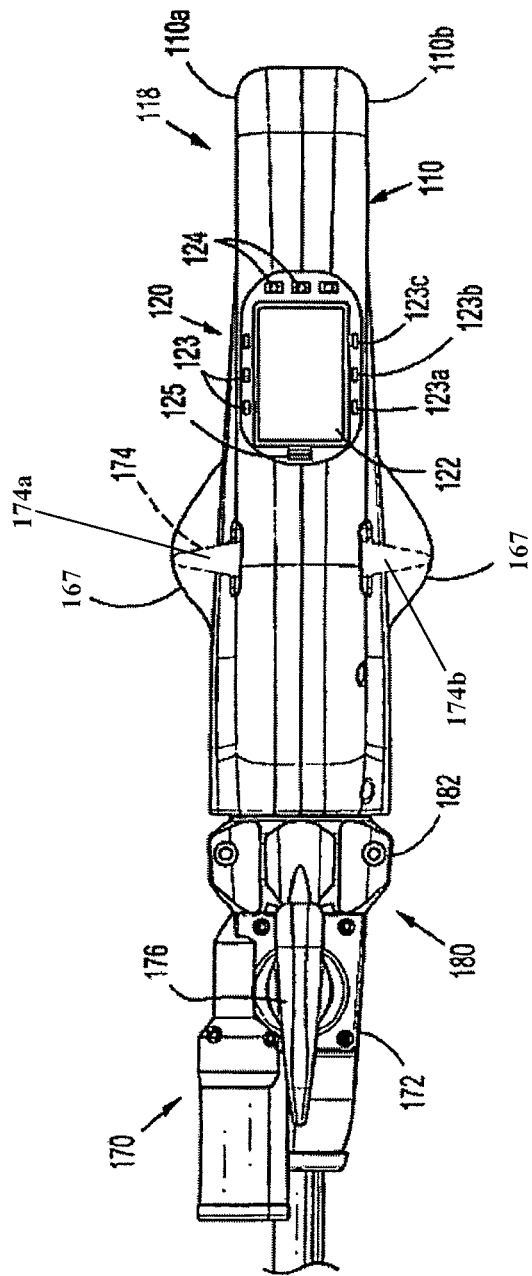
FIG. 3 is a top plan view of the powered surgical instrument of FIG. 2.

Referring to FIG. 3, a proximal area 118 of the housing 110 includes a user interface 120. The user interface 120 includes a screen 122 and a plurality of switches 124. The user interface 120 may display various types of operational parameters of the surgical instrument 10 such as "mode" (e.g., rotation, articulation or actuation). Operational parameters may be communicated to the user interface 120 via a sensor. Operational parameters may include "status" (e.g., speed of rotation, angle of articulation or type of actuation) and "feedback," such as whether staples have been fired based on the information reported by the sensors disposed in the surgical instrument 10. Error codes and other codes (e.g., improper loading, replace battery, battery level, and estimated number of firings remaining) may also be communicated to the user interface 120.

The screen 122 may be an LCD screen, a plasma screen, electroluminescent screen and the like. In one embodiment the screen 122 may be a touch screen, obviating the need for the switches 124. The touch screen may incorporate resistive, surface wave, capacitive, infrared, strain gauge, optical, dispersive signal or acoustic pulse recognition touch screen technologies. The touch screen may allow the user to provide input while viewing operational feedback. This approach may enable facilitation of sealing screen components to help sterilize the surgical instrument 10, as well as inhibiting particle and/or fluid contamination. In certain embodiments, the screen 122 is pivotably or rotatably mounted to the surgical instrument 10 for flexibility in viewing the screen 122 during use or preparation (e.g., via a hinge or ball-and-socket mount).

The switches 124 may be used for starting and/or stopping movement of the surgical instrument 10 as well as selecting the pivot direction, speed and/or torque. Also, at least one switch 124 may be used for selecting an emergency mode that overrides various settings. The switches 124 may also be used for selecting various options on the screen 122, such as responding to prompts while navigating user interface menus and selecting various settings, allowing a user to input different body tissue types and various sizes and lengths of staple cartridges.

The switches 124 may be formed from a micro-electronic tactile or non-tactile membrane, a polyester membrane, elastomer, plastic or metal keys of various shapes and sizes. Additionally, switches may be positioned at different heights from one another and/or may include raised indicia or other textural features (e.g., concavity or convexity) to allow a user to depress an appropriate switch without the need to look at user interface 120.

In addition to the screen 122, the user interface 120 may include one or more visual outputs 123 which may include one or more colored visible lights or light emitting diodes ("LEDs") to provide feedback to the user. The visual outputs 123 may include corresponding indicators of various shapes, sizes and colors having numbers and/or text which identify the visual outputs 123. The visual outputs 123 are disposed on top of the housing 110 such that the outputs 123 are raised and protrude in relation to the housing 110, providing for better visibility of the visual outputs 123.

The visual outputs 123 may be displayed in a certain combination to indicate a specific operational mode to the user. In one embodiment, the visual outputs 123 include a first light (e.g., yellow) 123a, a second light (e.g., green) 123b and a third light (e.g., red) 123c. The lights are operated in a particular combination associated with a particular operational mode. For example, the first light turned on and the second and third lights turned off may indicate that the loading unit 169 and staple cartridge are loaded and power is activated, allowing the end effector 160 to clamp as a grasper and articulate. In another embodiment, the visual output 123 may include a single multi-colored LED which displays a particular color associated with a particular operational mode.

The user interface 120 also includes audio outputs 125 (e.g., tones, bells, buzzers, and integrated speaker) to communicate various status changes to the user (e.g., low battery and empty cartridge). Audible feedback can be used in conjunction with or in lieu of the visual outputs 123. The audible feedback may be provided in the forms of clicks, snaps, beeps, rings, and buzzers in single or multiple pulse sequences. In one embodiment, a simulated mechanical sound may be prerecorded that replicates the click and/or snap sounds generated by mechanical lockouts and mechanisms of conventional non-powered instruments. This eliminates the need to generate these mechanical sounds through the actual components of the surgical instrument 10 and also avoids the use of beeps and other electronic sounds which are usually associated with other operating room equipment, thereby minimizing or eliminating confusion from extraneous audible feedback.

The surgical instrument 10 may also provide for haptic or vibratory feedback through a haptic mechanism (not explicitly shown) within the housing 110. The haptic feedback may be used in conjunction with the auditory and visual feedback or in lieu of it to avoid confusion with the operating room equipment which relies on audio and visual feedback. The haptic mechanism may be an asynchronous motor that vibrates in a pulsating manner. In one embodiment, the vibrations are at a frequency of about 30 Hz or above, providing a displacement having an amplitude of 1.5 mm or lower to limit the vibratory effects from reaching the loading unit 169.

The user interface 120 may also include different colors and/or intensities of text on the screen 122 and/or on the switches 124 for further differentiation between the displayed items. The visual, auditory or haptic feedback can be increased or decreased in intensity. For example, the intensity of the feedback may be used to indicate that the forces on the instrument are becoming excessive.

Figure 5:
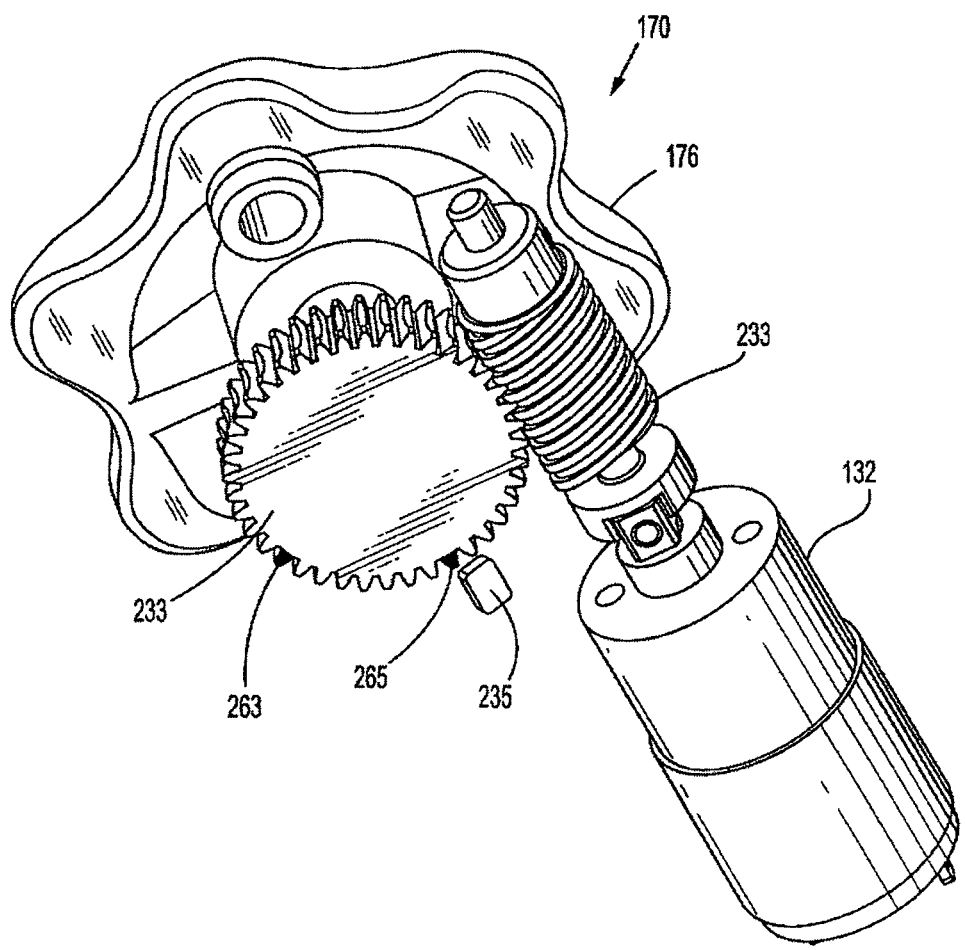
FIG. 5 is a perspective view of an articulation mechanism of the powered surgical instrument of FIG. 1 in accordance with an embodiment of the present disclosure.

FIGS. 1-5 illustrate an articulation mechanism 170, including an articulation housing 172, a powered articulation switch 174, an articulation motor 132 and a manual articulation knob 176. The articulation switch 174 may be a rocker and/or a slide switch having an arm 174a and 174b on each side of the housing 110 allowing for either right or left hand usage of the articulation switch 174. Translation of the powered articulation switch 174 or pivoting of the manual articulation knob 176 activates the articulation motor 132, which then actuates an articulation gear 233 of the articulation mechanism 170 as shown in FIG. 5. Actuation of articulation mechanism 170 causes the end effector 160 to move from its first position, where longitudinal axis B-B is substantially aligned with longitudinal axis A-A, towards a position in which longitudinal axis B-B is disposed at an angle to longitudinal axis A-A. Preferably, a plurality of articulated positions is achieved. The powered articulation switch 174 may also incorporate similar non-linear speed controls as the clamping mechanism as controlled by the switches 114a, 114b.

Further, the housing 110 includes switch shields 167 having a wing-like shape and extending from the top surface of the housing 110 over the switch 174. The switch shields 167 minimize accidental activation of the switch 174 when the surgical instrument 10 is placed down or from physical obstructions during use and require the user to reach below the shields 167 in order to activate the articulation mechanism 170.

Additionally, articulation housing 172 and powered articulation switch 174 are mounted to a rotating housing assembly 180. Rotation of a rotation knob 182 about first longitudinal axis A-A causes housing assembly 180 as well as articulation housing 172 and powered articulation switch 174 to rotate about first longitudinal axis A-A, and thus causes corresponding rotation of distal portion 224 of firing rod 220 (FIG. 6) and end effector 160 about first longitudinal axis A-A. The articulation mechanism 170 is electro-mechanically coupled to first and second conductive rings 157 and 159 which are disposed on the housing nose assembly 155 as shown in FIG. 4. The conductive rings 157 and 159 may be soldered and/or crimped onto the nose assembly 155 and are in electrical contact with the power source 400 thereby providing electrical power to the articulation mechanism 170. The nose assembly 155 may be modular (e.g., separate from the housing 110) and may be attached to the housing 110 during assembly to allow for easier soldering and/or crimping of the rings. The articulation mechanism 170 includes one or more brush and/or spring loaded contacts in contact with the conductive rings 157 and 159 such that, as the housing assembly 180 (FIG. 3) is rotated along with the articulation housing 172, the articulation mechanism 170 is in continuous contact with the conductive rings 157 and 159 thereby receiving electrical power from the power source 400.

Further details of articulation housing 172, powered articulation switch 174, manual articulation knob 176 and providing articulation to end effector 160 are described in detail in commonly-owned U.S. patent application Ser. No. 11/724,733 filed Mar. 15, 2007, the contents of which are hereby incorporated by reference in their entirety.

As illustrated in FIGS. 4 and 6, embodiments of the surgical instrument 10 include a motion sensor 251 that is electrically coupled (252) to the firing rod 220. The motion sensor 251 may sense the position of the firing rod 220 relative to the elongated shaft 140. The motion sensor 251 may be used alone or in combination with other sensors including limit switches, proximity sensors (e.g., optical and/or ferromagnetic), linear variable displacement transducers, and shaft encoders, which may be disposed within housing 110, to control and/or measure an articulation angle of end effector 160 and/or a position of the firing rod 220.

FIGS. 4-8 illustrate various internal components of the surgical instrument 10, including a drive motor 200, a drive tube 210, and a firing rod 220 having a proximal portion 222 and a distal portion 224. The drive tube 210 is rotatable about drive tube axis C-C. Drive motor 200 is disposed in mechanical cooperation with drive tube 210 and is configured to rotate the drive tube 210 about drive gear axis C-C. In one embodiment, the drive motor 200 may be an electrical motor or a gear motor, which may include gearing incorporated within its housing.

Firing rod coupling 190 provides a link between the proximal portion 222 and the distal portion 224 of the firing rod 220. Specifically, the firing rod coupling 190 enables rotation of the distal portion 224 of the firing rod 220 with respect to proximal portion 222 of firing rod 220. Thus, firing rod coupling 190 enables the proximal portion 222 of the firing rod 220 to remain non-rotatable, as discussed below with reference to an alignment plate 350, while allowing rotation of distal portion 224 of firing rod 220 (e.g., upon rotation of rotation knob 182).

Figure 7:
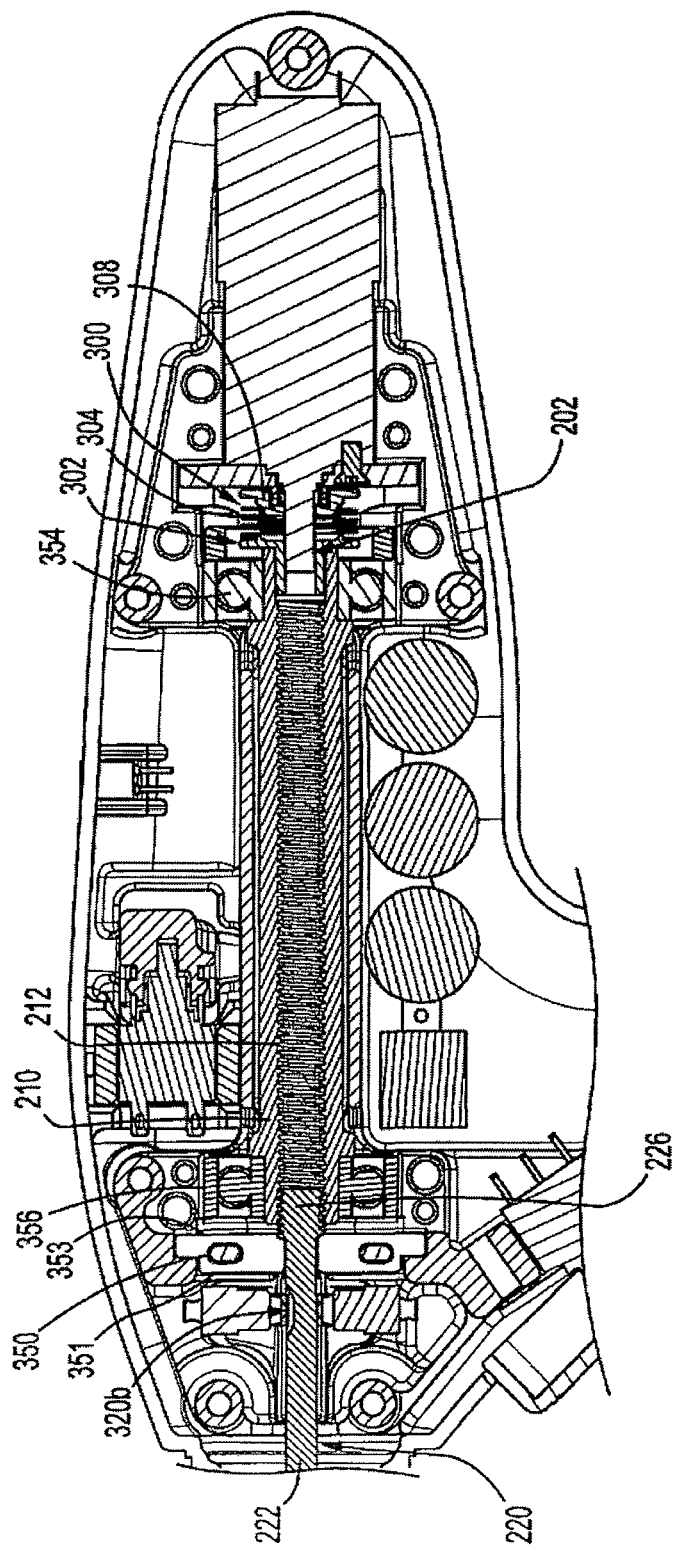
FIG. 7 is a partial cross-sectional view of the housing of the powered surgical instrument of FIG. 1 in accordance with another embodiment of the present disclosure.

With reference to FIGS. 6 and 7, the proximal portion 222 of firing rod 220 includes a threaded portion 226, which extends through an internally-threaded portion 212 of drive tube 210. This relationship between firing rod 220 and drive tube 210 causes firing rod 220 to move distally and/or proximally, in the directions of arrows D and E, along threaded portion 212 of drive tube 210 upon rotation of drive tube 210 in response to the rotation of the drive motor 200. As the drive tube 210 rotates in a first direction (e.g., clockwise), firing rod 220 moves proximally (i.e., in the direction of arrow E). As illustrated in FIG. 6, the firing rod 220 is disposed at its proximal-most position. As the drive tube 210 rotates in a second direction (e.g., counter-clockwise), firing rod 220 moves distally (i.e., in the direction of arrow D). As illustrated in FIG. 7, the firing rod 220 is disposed at its distal-most position.

The firing rod 220 is distally and proximally translatable within particular limits. Specifically, a first end 222a of proximal portion 222 of firing rod 220 acts as a mechanical stop in combination with an alignment plate 350. That is, upon retraction, when firing rod 220 is translated proximally, first end 222a contacts a distal surface 351 of alignment plate 350, thus inhibiting continued proximal translation of firing rod 220 as shown in FIG. 6. Additionally, the threaded portion 226 of the proximal portion 222 acts as a mechanical stop in combination with the alignment plate 350. That is, when firing rod 220 is translated distally, the threaded portion 226 contacts a proximal surface 353 of the alignment plate 350, thus inhibiting further distal translation of the firing rod 220 as shown FIG. 7.

The alignment plate 350 includes an aperture, which has a non-round cross-section. The non-round cross-section of the aperture inhibits rotation of the proximal portion 222 of the firing rod 220, thus limiting the proximal portion 222 of the firing rod 220 to axial translation through the aperture. Further, a proximal bearing 354 and a distal bearing 356 are disposed at least partially around drive tube 210 to facilitate the rotation of the drive tube 210, while helping align drive tube 210 within housing 110. The drive tube 210 includes a distal radial flange 210a and a proximal radial flange 210b on each end of the drive tube 210 which retain the drive tube 210 between the distal bearing 356 and the proximal bearing 354, respectively.

Figure 9:
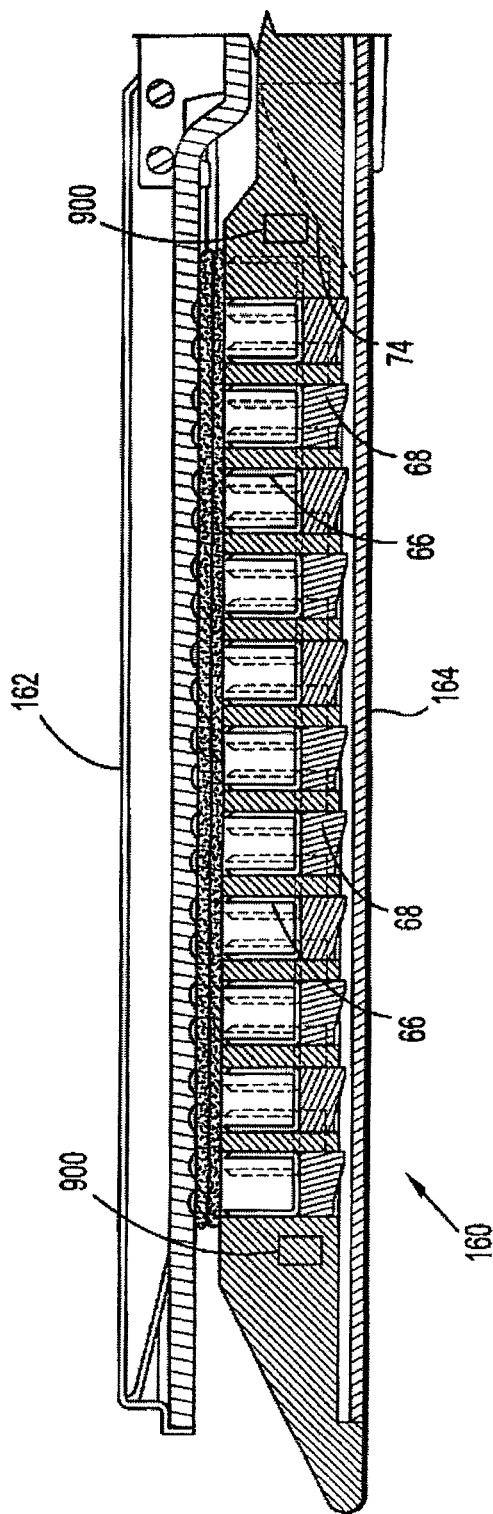
FIG. 9 is a side cross-sectional view of an end effector of the powered surgical instrument of FIG. 1.

Rotation of drive tube 210 in a first direction (e.g., counter-clockwise) corresponds to distal translation of the firing rod 220, which actuates jaw members 162, 164 of the end effector 160 to grasp or clamp tissue. Additional distal translation of firing rod 220 ejects surgical fasteners from the end effector 160 to fasten tissue by actuating cam bars and/or an actuation sled 74 (FIG. 9). Further, the firing rod 220 may also be configured to actuate a knife (not explicitly shown) to sever tissue. Proximal translation of firing rod 220 corresponding with rotation of the drive tube 210 in a second direction (e.g., clockwise) actuates the anvil and cartridge assemblies 162, 164 (FIG. 9) and/or knife to retract or return to corresponding pre-fired positions. Further details of firing and otherwise actuating end effector 160 are described in detail in commonly-owned U.S. Pat. No. 6,953,139 to Milliman et al. (the '139 patent), the entire disclosure of which is hereby incorporated by reference.

Figure 8:
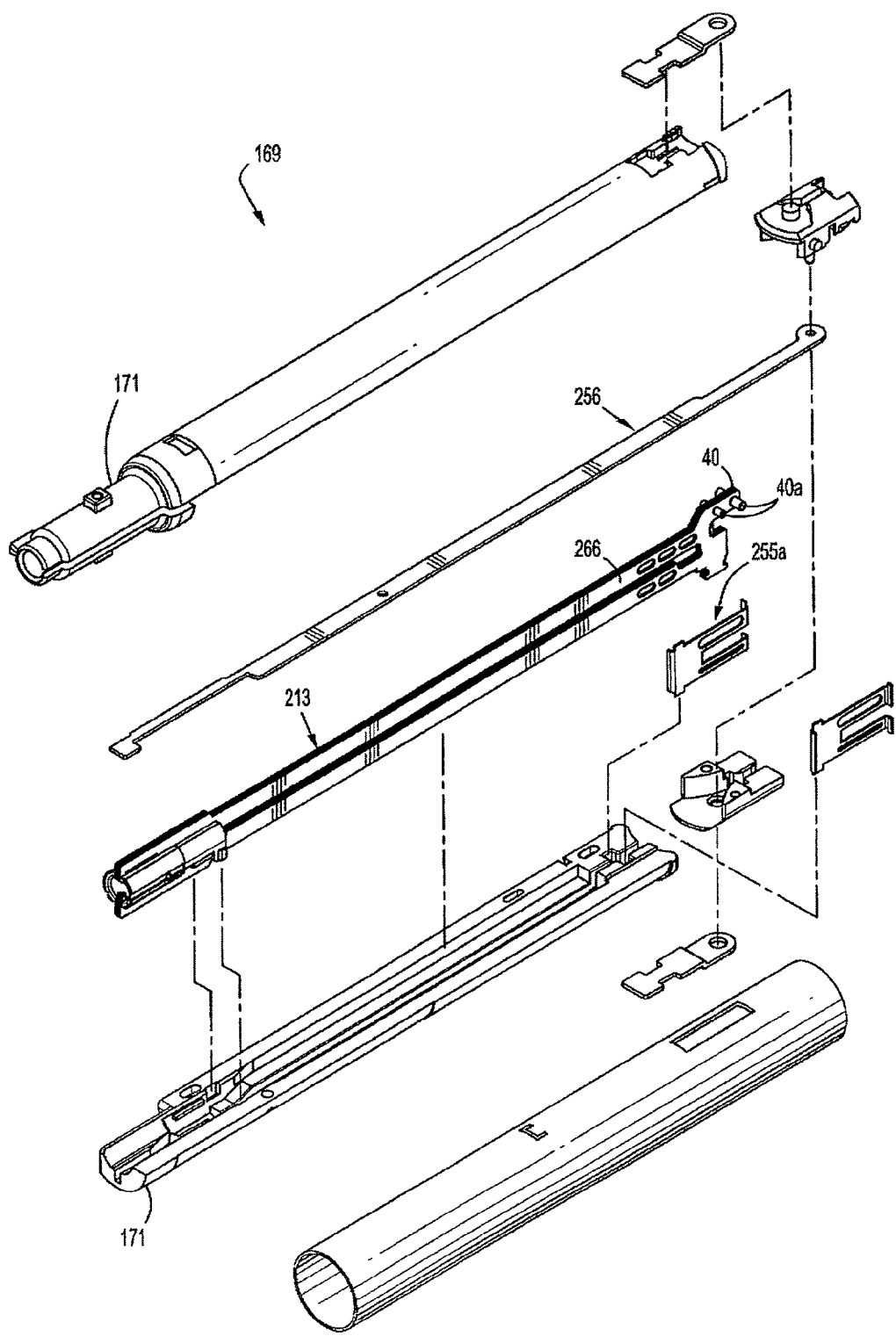
FIG. 8 is an exploded perspective view of the mounting assembly and the proximal body portion of a loading unit with parts separated of the powered surgical instrument of FIG. 1.

FIG. 8 shows an exploded view of the loading unit 169. The end effector 160 may be actuated by an axial drive assembly 213 having a drive beam or drive member 266. The distal end of the drive beam 213 may include a knife blade. In addition, the drive beam 213 includes a retention flange 40 having a pair of cam members 40a, which engage the anvil and cartridge assemblies 162, 164 during advancement of the drive beam 213 longitudinally. The drive beam 213 advances an actuation sled 74 longitudinally through the staple cartridge 164. As shown in FIG. 9, the sled 74 has cam wedges for engaging pushers 68 disposed in slots of the cartridge assembly 164, as the sled 74 is advanced. Staples 66 disposed in the slots are driven through tissue and against the anvil assembly 162 by the pushers 66.

Figure 10:
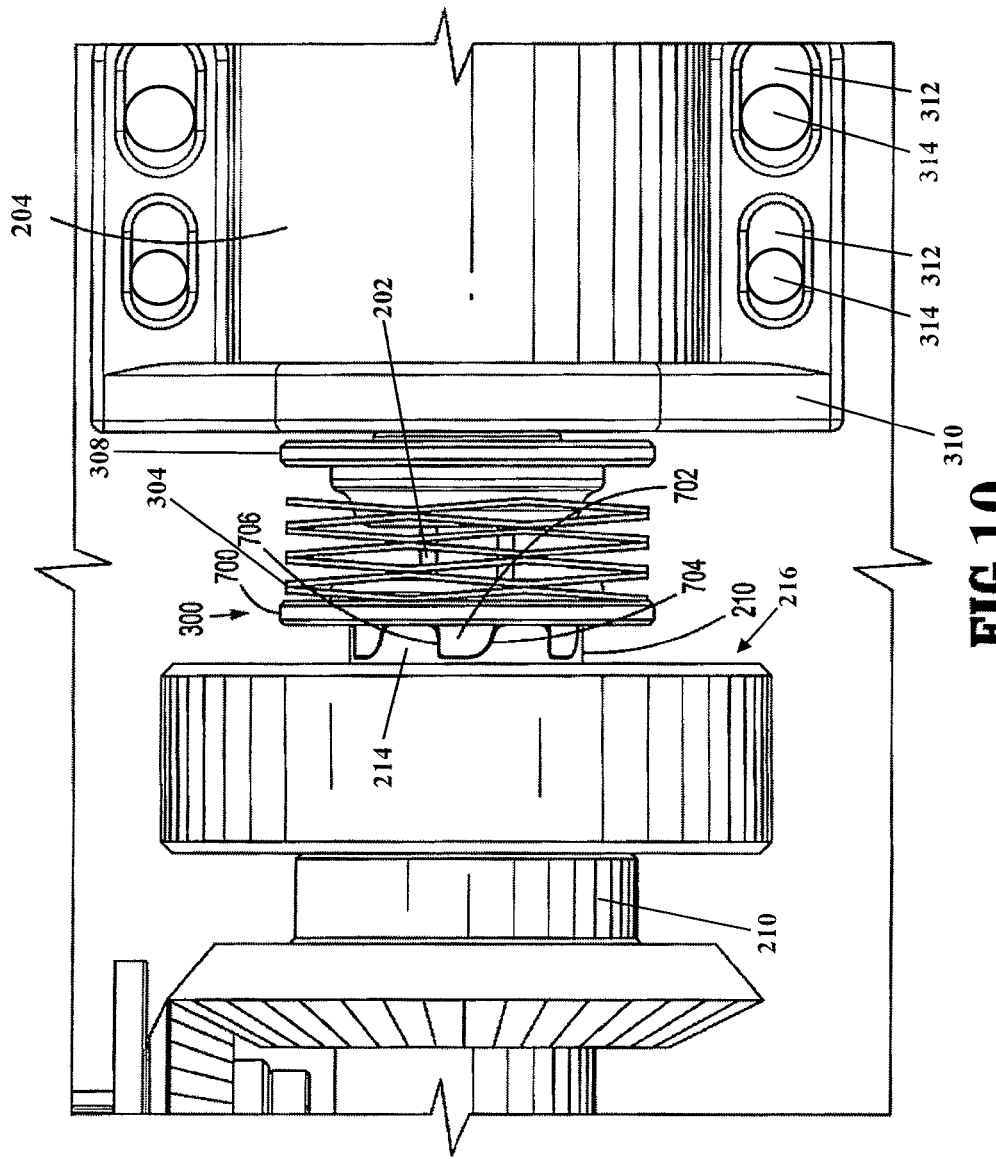
FIG. 10 is a partial side view showing a clutch of the powered surgical instrument of FIG. 1.

With reference to FIG. 10, a drive motor shaft 202 is shown extending from a planetary gear 204 that is attached to the drive motor 200. The drive motor shaft 202 mechanically cooperates with the clutch 300. The drive motor shaft 202 is rotated by the drive motor 200, thus resulting in rotation of clutch 300. The clutch 300 includes a clutch plate 700 and a spring 304 and is shown having wedged portions 702 disposed on the clutch plate 700, which are configured to mate with an interface (e.g., wedges 214) disposed on a proximal face 216 of the drive tube 210.

Spring 304 is illustrated between planetary gear 204 and the drive tube 210. Specifically, and in accordance with the embodiment illustrated in FIG. 10, spring 304 is illustrated between the clutch plate 700 and a clutch washer 308. Additionally, drive motor 200 and planetary gear 204 are mounted on a motor mount 310. As illustrated in FIG. 10, motor mount 310 is adjustable proximally and distally with respect to housing 110 via slots 312 disposed in motor mount 310 and protrusions 314 disposed on the housing 110.

In an embodiment of the disclosure, the clutch 300 is implemented as a slip unidirectional clutch to limit torque and high inertial loads on the drive components. Wedged portions 702 of the clutch 300 are configured and arranged to slip with respect to the wedges 214 of the proximal face 216 of the drive tube 210 unless a threshold force is applied to the clutch plate 700 via the clutch spring 304. Further, when spring 304 applies the threshold force needed for the wedged portions 702 and wedges 214 to engage without slipping, the drive tube 210 will rotate upon rotation of drive motor 200. The wedged portions 702 and/or wedges 214 may be configured to slip in one and/or both directions (i.e., clockwise and/or counter-clockwise) with respect to one another when a firing force is attained on the firing rod 220.

Figure 11:
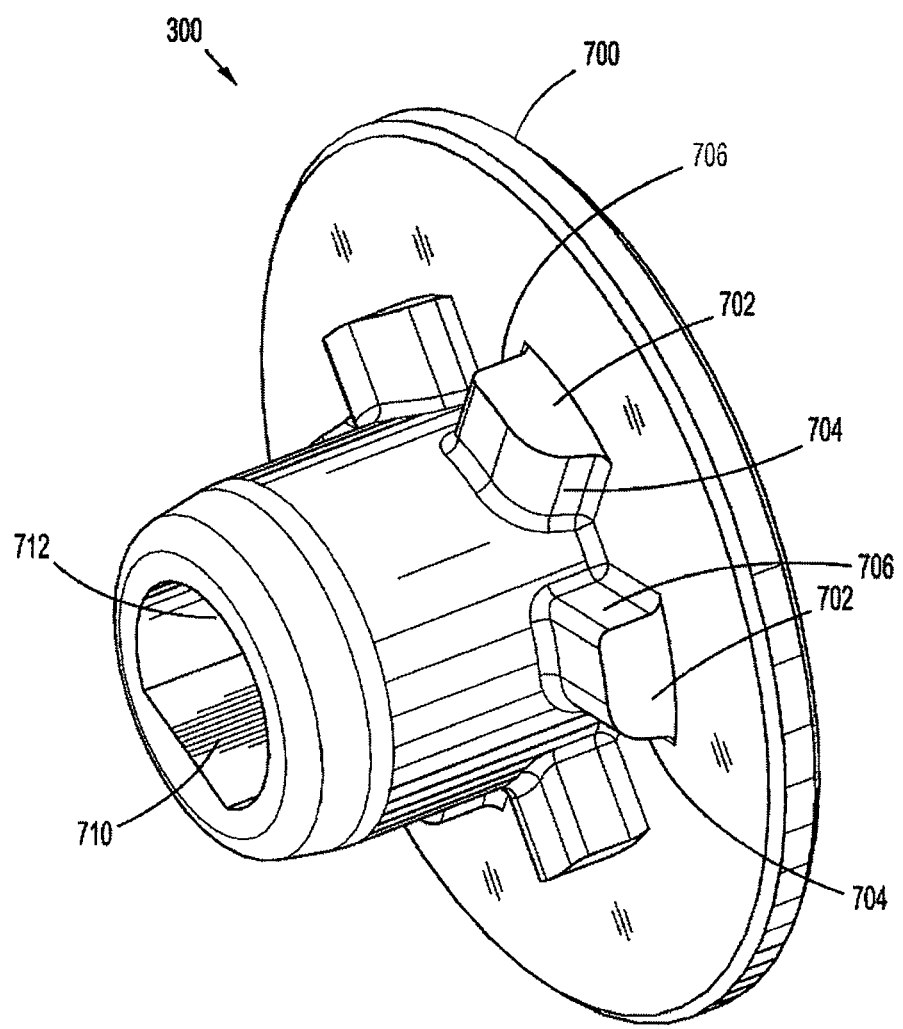
FIG. 11 is a perspective view of a unidirectional clutch plate of the powered surgical instrument of FIG. 1.

As illustrated in FIGS. 10 and 11, the clutch 300 is shown with a unidirectional clutch plate 700. The clutch plate 700 includes a plurality of wedged portions 702 having a slip face 704 and a grip face 706. The slip face 704 has a curved edge which engages the wedges 214 of the drive tube 210 up to a predetermined load. The grip face 706 has a flat edge which fully engages the drive tube 210 and inhibits slippage.

When the clutch plate 700 is rotated in a first direction (e.g., clockwise), the grip face 706 of the wedged portions 702 engage the wedges 214 without slipping, providing for full torque from the drive motor 200. When the clutch plate 700 is rotated in a reverse direction (e.g., counterclockwise) the slip face 704 of the wedged portions 702 engage the wedges 214 and limit the torque being transferred to the drive tube 210. Thus, if the load being applied to the slip face 704 is over the limit, the clutch 300 slips and the drive tube 210 is not rotated. This inhibits high load damage to the end effector 160 or tissue which can occur due to the momentum and dynamic friction of the drive components. More specifically, the drive mechanism of the surgical instrument 10 can drive the firing rod 220 in a forward direction with less torque than in reverse. Use of a unidirectional clutch eliminates this problem. In addition electronic clutch may also be used to increase the motor potential during retraction (e.g., driving the firing rod 220 in reverse along with the drive motor 200, drive tube 210, clutch assembly 300, alignment plate 350, and any portion of the firing rod 220) as discussed in more detail below.

Drive motor shaft 202 may include a D-shaped cross-section 708, which includes a substantially flat portion 710 and a rounded portion 712. Thus, while drive motor shaft 202 is translatable with respect to clutch plate 700, drive motor shaft 202 will not "slip" with respect to clutch plate 700 upon rotation of drive motor shaft 202. That is, rotation of drive motor shaft 202 will result in a slip-less rotation of clutch plate 700.

The loading unit, in certain embodiments according to the present disclosure, includes an axial drive assembly that cooperates with firing rod 220 to approximate anvil assembly 162 and cartridge assembly 164 of end effector 160, and fire staples from the staple cartridge. The axial drive assembly may include a beam that travels distally through the staple cartridge and may be retracted after the staples have been fired, as discussed above and as disclosed in certain embodiments of the '139 Milliman patent.

With reference to FIG. 4, the surgical instrument 10 includes a power source 400 which may be a rechargeable battery (e.g., lead-based, nickel-based, or lithium-ion based). The power source 400 may include at least one disposable battery. The disposable battery may be between about 9 volts and about 30 volts.

The power source 400 includes one or more battery cells 401 depending on the current load needs of the surgical instrument 10. Further, the power source 400 includes one or more ultracapacitors 402 which act as supplemental power storage due to their much higher energy density than conventional capacitors. Ultracapacitors 402 can be used in conjunction with the cells 401 during high energy draw. The ultracapacitors 402 can be used for a burst of power when energy is desired/required more quickly than can be provided solely by the cells 401 (e.g., when clamping thick tissue, rapid firing, clamping, etc.), as cells 401 are typically slow-drain devices from which current cannot be quickly drawn. This configuration can reduce the current load on the cells thereby reducing the number of the cells 401 and/or extending the life of the cells 401. The cells 401 may be connected to the ultracapacitors 402 to charge the capacitors.

The power source 400 may be removable along with the drive motor 200 to provide for recycling of these components and reuse of the surgical instrument 10. In another embodiment, the power source 400 may be an external battery pack, which is worn on a belt and/or harness by the user and wired to the surgical instrument 10 during use.

The power source 400 is enclosed within an insulating shield 404 which may be formed from an absorbent, flame resistant and retardant material. The shield 404 electrically and thermally isolates components of the surgical instrument 10 from the power source 400. More specifically, the shield 400 inhibits heat generated by the power source 400 from heating other components of the surgical instrument 10. In addition, the shield 404 may also be configured to absorb any chemicals or fluids which may leak from the cells 402 during heavy use and/or damage.

The power source 400 is coupled to a power adapter 406 which is configured to connect to an external power source (e.g., DC transformer). The external power source may be used to recharge the power source 400 or provide for additional power requirements. The power adapter 406 may also be configured to interface with electrosurgical generators which can then supply power to the surgical instrument 10. In this configuration, the surgical instrument 10 also includes an AC-to-DC power source which converts RF energy from the electrosurgical generators and powers the surgical instrument 10.

In another embodiment the power source 400 is recharged using an inductive charging interface. The power source 400 is coupled to an inductive coil (not explicitly shown) disposed within the proximal portion of the housing 110. Upon being placed within an electromagnetic field, the inductive coil converts the energy into electrical current that is then used to charge the power source 400. The electromagnetic field may be produced by a base station (not explicitly shown) that is configured to interface with the proximal portion of the housing 110, such that the inductive coil is enveloped by the electromagnetic field. This configuration eliminates the need for external contacts and allows for the proximal portion of the housing 110 to seal the power source 400 and the inductive coil within a water-proof environment which inhibits exposure to fluids and contamination.

With reference to FIG. 6, the surgical instrument 10 also includes one or more safety circuits such as a discharge circuit 410 and a motor and battery operating module 412. For clarity, wires and other circuit elements interconnecting various electronic components of the surgical instrument 10 are not shown, but such wires and other circuit elements are contemplated by the present disclosure. Certain components of the surgical instrument 10 communicate wirelessly.

The discharge circuit 410 is coupled to a switch 414 and a resistive load 417 which, in turn, are coupled to the power source 400. The switch 414 may be a user-activated or an automatic (e.g., timer, counter) switch which is activated when the power source 400 needs to be fully discharged for a safe and low temperature disposal (e.g., at the end of surgical procedure). Once the switch 414 is activated, the load 417 is electrically connected to the power source 400 such that the potential of the power source 400 is directed to the load 417. The automatic switch may be a timer or a counter which is automatically activated after a predetermined operational time period or number of uses to discharge the power source 400. The load 417 has a predetermined resistance sufficient to fully and safely discharge all of the cells 401.

The motor and battery operating module 412 is coupled to one or more thermal sensors 413 which determine the temperature within the drive motor 200 and the power source 400 to ensure safe operation of the surgical instrument 10. The sensors may be an ammeter for determining the current draw within the power source 400, a thermistor, a thermopile, a thermocouple, a thermal infrared sensor and the like. Monitoring temperature of these components allows for a determination of the load being placed on these components. The increase in the current flowing through these components causes an increase in the temperature of these components. The temperature and/or current draw data may then be used to control the power consumption in an efficient manner or assure safe levels of operation.

To ensure safe and reliable operation of the surgical instrument 10, it is desirable to ensure that the power source 400 is authentic and/or valid (e.g., conforms to strict quality and safety standards) and is operating within a predetermined temperature range. Authentication that the power source 400 is valid minimizes risk of injury to the patient and/or the user due to poor quality.

Referring again to FIGS. 4 and 6, some embodiments of the surgical instrument may include, in addition to the motion sensor 251, a plurality of sensors for providing feedback information relating to the function of the surgical instrument 10. Any combination of sensors may be disposed within the surgical instrument 10 to determine its operating stage, such as, staple cartridge load detection as well as its status, articulation, clamping, rotation, stapling, cutting and retracting, and the like. The sensors can be actuated by proximity, displacement or contact of various internal components of the surgical instrument 10 (e.g., firing rod 220 and drive motor 200).

In the illustrated embodiments, the sensors can be rheostats (e.g., variable resistance devices), current monitors, conductive sensors, capacitive sensors, inductive sensors, thermal-based sensors, limit actuated switches, multiple position switch circuits, pressure transducers, linear and/or rotary variable displacement transducers, linear and/or rotary potentiometers, optical encoders, ferromagnetic sensors, Hall Effect sensors, and proximity switches. The sensors measure rotation, velocity, acceleration, deceleration, linear and/or angular displacement, detection of mechanical limits (e.g., stops), etc. This is attained by implementing multiple indicators arranged in either linear or rotational arrays on the mechanical drive components of the surgical instrument 10. The sensors then transmit the measurements to the microcontroller 500 which determines the operating status of the surgical instrument 10. In addition, the microcontroller 500 also adjusts the motor speed or torque of the surgical instrument 10 based on the measured feedback.

Figure 12:
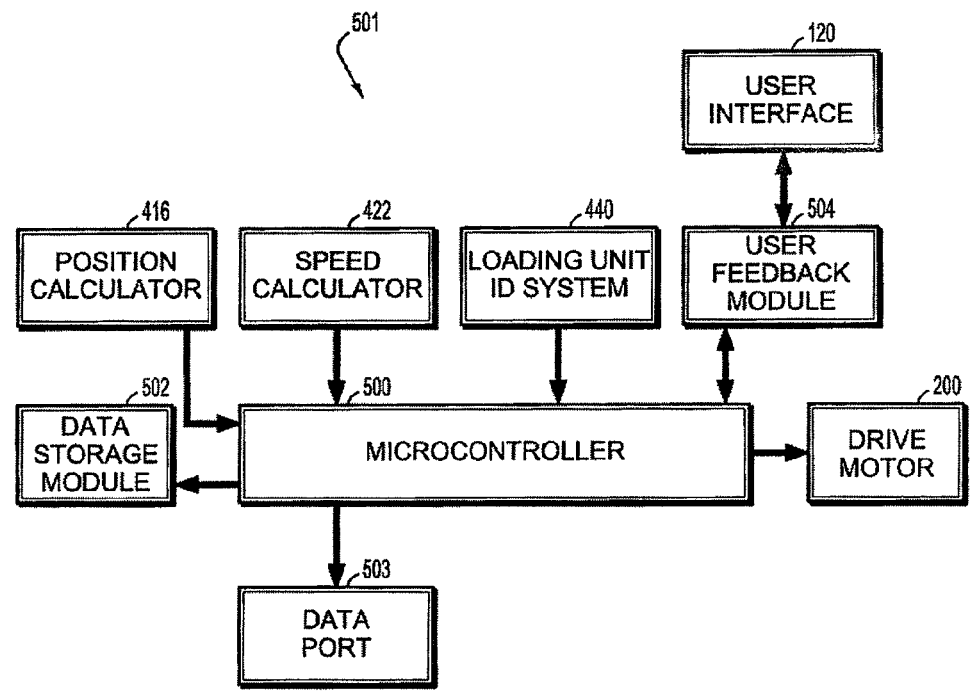
FIG. 12 is a schematic diagram of a control system in accordance with an embodiment of the present disclosure.

In embodiments where the clutch 300 is implemented as a slip clutch as shown in FIGS. 11 and 12, linear displacement sensors (e.g., motion sensor 251 in FIGS. 4 and 6) are positioned distally of the clutch 300 to provide accurate measurements. In this configuration, slippage of the clutch 300 does not affect the position, velocity and acceleration measurements recorded by the sensors.

With reference to FIG. 4, a load switch 230 is disposed within the articulation housing 172. The switch 230 is connected in series with the switch 114, inhibiting activation of the surgical instrument 10 unless the loading unit 169 (FIG. 1) is properly loaded into the surgical instrument 10. If the loading unit 169 is not loaded into the surgical instrument 10, the main power switch (e.g., switch 114) is open, thereby inhibiting use of any electronic or electric components of the surgical instrument 10. This also inhibits any possible current draw from the power source 400 allowing the power source 400 to maintain a maximum potential over its specified shelf life.

Thus, the switch 230 acts as a so-called "lock-out" switch which inhibits false activation of the surgical instrument 10 since the switch is inaccessible to external manipulation and can only be activated by the insertion of the loading unit 169. The switch 230 is activated by displacement of a plunger or sensor tube as the loading unit 169 is inserted into the elongated shaft 140. Once the switch 230 is activated, the power from the power source 400 is supplied to the electronic components (e.g., sensors, microcontroller 500, etc.) of the surgical instrument 10 providing the user with access to the user interface 120 and other inputs/outputs. This also activates the visual outputs 123 to light up according to the light combination indicative of a properly loaded loading unit 169 wherein all the lights are off as described in Table 1.

Once the loading unit 169 is inserted into the elongated shaft, the switch 230 also determines whether the loading unit 169 is loaded correctly based on the position thereof. If the loading unit 169 is improperly loaded, the switch 114 is not activated and an error code is relayed to the user via the user interface 120 (e.g., all the lights are off as described in Table 1). If the loading unit 169 has already been fired, any mechanical lockouts have been previously activated or the staple cartridge has been used, the surgical instrument 10 relays the error via the user interface 120, e.g., the first light 123a is flashing.

In one embodiment, a second lock-out switch 259 (FIG. 4) coupled to the main switch 114 may be implemented in the surgical instrument 10 as a bioimpedance, capacitance or pressure sensor disposed on the top surface of the handle portion 112 configured to be activated when the user grasps the surgical instrument 10. Thus, unless the surgical instrument 10 is grasped properly, the operation of the switch 114 is disabled.

Referring to FIG. 6, the surgical instrument 10 includes a position calculator 416 for determining and outputting the current linear position of the firing rod 220. The position calculator 416 is electrically coupled to the motion sensor 251, which, in some embodiments, senses the markings on the firing rod 220 using a light emitter and detector unit. The position calculator 416 calculates the current linear position of the firing rod 220 based on a sensor signal output from the motion sensor 251.

In some embodiments, the position calculator 416 may be electrically coupled to other supplemental sensors including a linear displacement sensor 237 and a rotation speed detecting apparatus 418 that is coupled to the drive motor 200. The rotation speed apparatus 418 includes an encoder 420 coupled to the motor for producing two or more encoder pulse signals in response to the rotation of the drive motor 200. The encoder 420 transmits the pulse signals to the apparatus 418, which then determines the rotational speed of the drive motor 200. The position calculator 416 thereafter determines the linear speed and position of the firing rod based on the rotational speed of the drive motor 200 since the rotation speed is directly proportional to the linear speed of the firing rod 220. The position calculator 416 and the speed calculator 422 are in communication with the microcontroller 500, which controls the drive motor 200 in response to the sensed feedback from the position and speed calculators 416, 422.

The surgical instrument 10 may include first and second indicators 320a, 320b disposed on the firing rod 220, which determine the speed of firing rod 220 and the location of firing rod 220 with respect to drive tube 210 and/or housing 110. For instance, a limit switch may be activated (e.g., shaft start position sensor 231 and clamp position sensor 232) by sensing first and second indicators 320a and/or 320b (e.g., bumps, grooves, indentations, etc.) passing thereby to determine position of firing rod 220, speed of firing rod 220 and mode of the surgical instrument 10 (e.g., clamping, grasping, firing, sealing, cutting, retracting). Further, the feedback received from first and second indicators 320a, 320b may be used to determine when firing rod 220 should stop its axial movement (e.g., when drive motor 200 should cease) depending on the size of the particular loading unit attached thereto.

More specifically, as the firing rod 220 is moved in the distal direction from its resting (e.g., initial) position, the first actuation of the position sensor 231 is activated by the first indicator 320a which denotes that operation of the surgical instrument 10 has commenced. As the operation continues, the firing rod 220 is moved further distally to initiate clamping, which moves first indicator 320a to interface with clamp position sensor 232. Further advancement of the firing rod 220 moves the second indicator 320b to interface with the position sensor 232 which indicates that the surgical instrument 10 has been fired.

As discussed above, the position calculator 416 is coupled to a linear displacement sensor 237 disposed adjacent to the firing rod 220. In one embodiment, the linear displacement sensor 237 may be a magnetic sensor. The firing rod 220 may be magnetized or may include magnetic material therein. The magnetic sensor may be a ferromagnetic sensor or a Hall Effect sensor which is configured to detect changes in a magnetic field. As the firing rod 220 is translated linearly due to the rotation of the drive motor 200, the change in the magnetic field in response to the translation motion is registered by the magnetic sensor. The magnetic sensor transmits data relating to the changes in the magnetic field to the position calculator 416 which then determines the position of the firing rod 220 as a function of the magnetic field data.

In one embodiment, a portion of the firing rod 220 may be magnetized. For example, the threads of the internally-threaded portion 212 or other notches (e.g., indicators 320a and/or 320b) disposed on the firing rod 220 may include or be made from a magnetic material. This allows for correlation of the cyclical variations in the magnetic field with each discrete translation of the threads as the magnetized portions of the firing rod 220 are linearly translated. The position calculator 416 thereafter determines the distance and the position of the firing rod 220 by summing the number of cyclical changes in the magnetic field and multiplies the sum by a predetermined distance between the threads (e.g., the screw pitch) and/or notches.

In one embodiment, the position calculator 416 is coupled to one or more switches 421 which are actuated by the threads of the internally-threaded portion 212 or the indicators 320a and/or 320b as the firing rod 220 and the firing rod coupling 190 are moved in the distal direction. The position calculator 416 counts the number of threads which activated the switch 421 and then multiplies the number by a predetermined distance between the threads (e.g., the screw pitch) or the indicators 320a and/or 320b.

The surgical instrument 10 also includes a speed calculator 422 which determines the current speed of a linearly moving firing rod 220 and/or the torque being provided by the drive motor 200. The speed calculator 422 is coupled to the motion sensor 251, which allows the speed calculator 422 to determine the speed of the firing rod 220 based on the rate of change of the displacement of the firing rod 220.

In one embodiment, the speed calculator 422 is further coupled to the rotation speed detecting apparatus 424 which includes the encoder 426. The encoder 426 transmits the pulses correlating to the rotation of the drive motor 200 which the speed calculator 422 then uses to calculate the linear speed of the firing rod 220. In another embodiment, the speed calculator 422 is coupled to a rotational sensor 239 which detects the rotation of the drive tube 210, thus, measuring the rate of rotation of the drive tube 210 which allows for determination of the linear velocity of the firing rod 220.

The speed calculator 422 is also coupled to a voltage sensor 428 which measures the back electromotive force ("EMF") induced in the drive motor 200. The back EMF voltage of the drive motor 200 is directly proportional to the rotational speed of the drive motor 200 which, as discussed above, is used to determine the linear speed of the firing rod 220.

Monitoring of the speed of the drive motor 200 can also be accomplished by measuring the voltage across the terminals thereof under constant current conditions. An increase in a load of the drive motor 200 yields a decrease in the voltage applied at the motor terminals, which is directly related to the decrease in the speed of the motor. Thus, measuring the voltage across the drive motor 200 provides for determining the load being placed thereon. In addition, by monitoring the change of the voltage over time (dV/dt), the microcontroller 500 can detect a quick drop in voltage which correlates to a large change in the load or an increase in temperature of the drive motor 200 and/or the power source 400.

In a further embodiment, the speed calculator 422 is coupled to a current sensor 430 (e.g., an ammeter). The current sensor 430 is in electrical communication with a shunt resistor 432 which is coupled to the drive motor 200. The current sensor 430 measures the current being drawn by the drive motor 200 by measuring the voltage drop across the resistor 432. Since the current used to power the drive motor 200 is proportional to the rotational speed of the drive motor 200 and, hence, the linear speed of the firing rod 220, the speed calculator 422 determines the speed of the firing rod 220 based on the current draw of the drive motor 200.

The current sensor 430 may also be coupled to the power source 400 to determine the current draw thereof which allows for analysis of the load on the end effector 160. This may be indicative of the tissue type being stapled since various tissue have different tensile properties which affect the load being exerted on the surgical instrument 10 and the power source 400 and/or the motor 200.

The speed calculator 422 may also be coupled to a second voltage sensor (not explicitly shown) for determining the voltage within the power source 400 thereby calculating the power draw directly from the source. In addition, the change in current over time (dI/dt) can be monitored to detect quick spikes in the measurements which correspond to a large increase in applied torque by the drive motor 200. Thus, the current sensor 430 is used to determine the speed and the load of the drive motor 200.

In addition, the velocity of the firing rod 220 as measured by the speed calculator 422 them may be compared to the current draw of the drive motor 200 to determine whether the drive motor 200 is operating properly. Namely, if the current draw is not commensurate (e.g., large) with the velocity (e.g., low) of the firing rod 220 then the motor 200 is malfunctioning (e.g., locked, stalled, etc.). If a stall situation is detected, or the current draw exceeds predetermined limits, the position calculator 416 then determines whether the firing rod 220 is at a mechanical stop. If this is the case, then the microcontroller 500 can shut down the drive motor 200 or enters a pulse and/or pause mode (e.g., discontinuous supply of power to the drive motor 200) to unlock the surgical instrument 10 and retract the firing rod 220.

In one embodiment, the speed calculator 422 compares the rotation speed of the drive tube 210 as detected by the rotation sensor 239 and that of the drive motor 200 based on the measurements from and the rotation speed detecting apparatus 424. This comparison allows the speed calculator 422 to determine whether there is clutch activation problem (e.g., slippage) if there is a discrepancy between the rotation of the clutch 300 and that of the drive tube 210. If slippage is detected, the position calculator 416 then determines whether the firing rod 220 is at a mechanical stop. If this is the case, then the microcontroller 500 can shut down the surgical instrument 10 or enter a pulse and/or pause mode (e.g., discontinuous supply of power to the drive motor 200), or retract the firing rod 220.

In addition to linear and/or rotational displacement of the firing rod 220 and other drive components, the surgical instrument 10 also includes sensors adapted to detect articulation of the end effector 160. With reference to FIG. 4, the surgical instrument 10 includes a rotation sensor 241 adapted to indicate the start position, the rotational direction and the angular displacement of the rotating housing assembly 180 at the start of the procedure as detected by the shaft start position sensor 231. The rotation sensor 241 operates by counting the number of indicators disposed on the inner surface of the rotation knob 182 by which the rotation knob 182 has been rotated.

With reference to FIG. 1, the present disclosure provides a loading unit identification system 440 which allows the surgical instrument 10 to identify the loading unit 169 and to determine operational status thereof. The identification system 440 provides information to the surgical instrument 10 on staple size, cartridge length, type of the loading unit 169, status of cartridge, proper engagement, and the like. This information allows the instrument to adjust clamping forces, speed of clamping and firing and end of stroke for various length staple cartridges.

Figure 14:
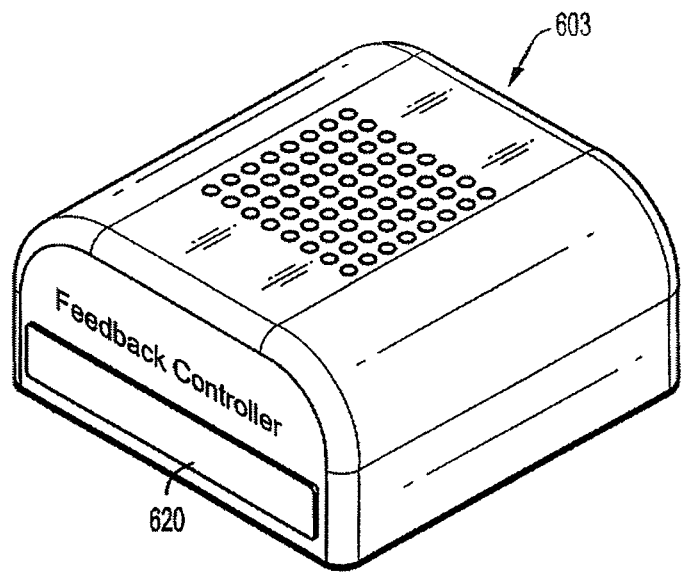
FIGS. 14-15 are perspective front and rear views of a feedback controller of the feedback control system in accordance with an embodiment of the present disclosure.
Figure 15:
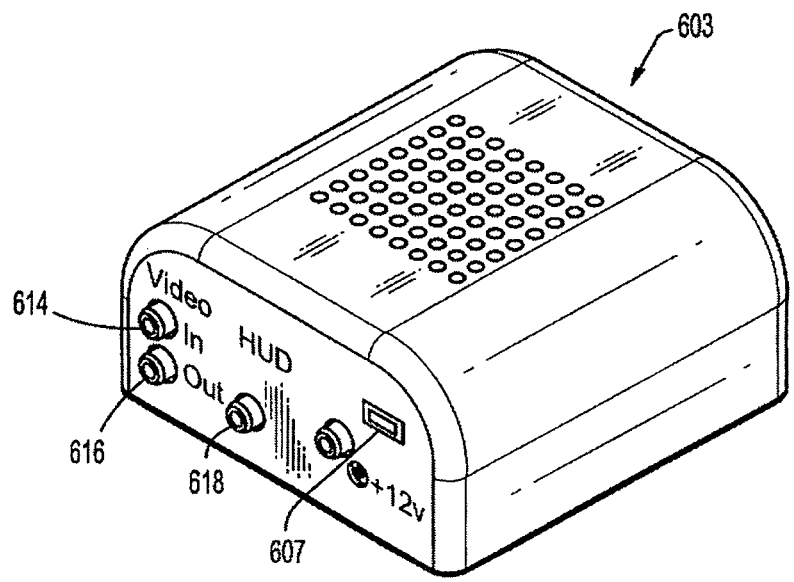
Figure 16:
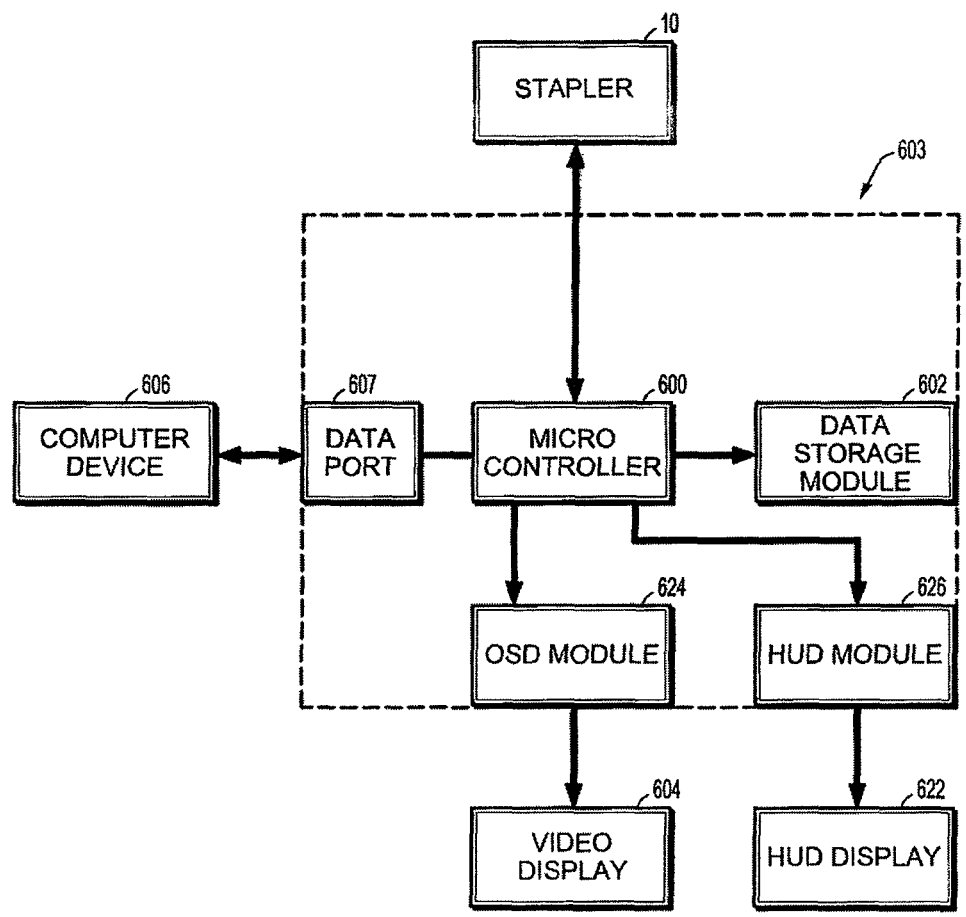
FIG. 16 is a schematic diagram of the feedback controller in accordance with an embodiment of the present disclosure.

The loading unit identification system 440 may also be adapted to determine and communicate to the surgical instrument 10 (e.g., a control system 501 shown in FIG. 12) various information, including the speed, power, torque, clamping, travel length and strength limitations for operating the particular end effector 160. The control system 501 may also determine the operational mode and adjust the voltage, clutch spring loading and stop points for travel of the components. More specifically, the identification system may include a component (e.g., a microchip, emitter or transmitter) disposed in the end effector 160 that communicates (e.g., wirelessly, via infrared signals, etc.) with the control system 501, or a receiver therein. A signal may be sent via firing rod 220, such that firing rod 220 functions as a conduit for communications between the control system 501 and end effector 160. In another embodiment, the signals can be sent through an intermediate interface, such as a feedback controller 603 (FIGS. 14-16).

By way of example, the sensors discussed above, including the motion sensor 251, may be used to determine if the staples have been fired from the staple cartridge, whether they have been fully fired, whether and the extent to which the beam has been retracted proximally through the staple cartridge and other information regarding the operation of the loading unit. In certain embodiments of the present disclosure, the loading unit incorporates components for identifying the type of loading unit, and/or staple cartridge loaded on the surgical instrument 10, including infra red, cellular, or radio frequency identification chips. The type of loading unit and/or staple cartridge may be received by an associated receiver within the control system 501, or an external device in the operating room for providing feedback, control and/or inventory analysis.

Information can be transmitted to the surgical instrument 10 via a variety of communication protocols (e.g., wired or wireless) between the loading unit 169 and the surgical instrument 10. The information can be stored within the loading unit 169 in a microcontroller, microprocessor, non-volatile memory, radio frequency identification tags, and identifiers of various types such as optical, color, displacement, magnetic, electrical, binary and gray coding (e.g., conductance, resistance, capacitance, impedance).

In one embodiment, the loading unit 169 and the surgical instrument 10 include corresponding wireless transceivers, an identifier 442 and an interrogator 444, respectively (FIG. 1). The identifier 442 includes memory or may be coupled to a microcontroller (e.g., microcontroller 500) for storing various identification and status information regarding the loading unit 169. Once the loading unit 169 is coupled to the surgical instrument 10, the surgical instrument 10 interrogates the identifier 442 via the interrogator 444 for an identifying code. In response to the interrogatory, the identifier 442 replies with the identifying code corresponding to the loading unit 169. During operation, once identification has occurred, the identifier 442 is configured to provide the surgical instrument 10 with updates as to the status of the loading unit 169 (e.g., mechanical and/or electrical malfunction, position, articulation, etc.).

The identifier 442 and the interrogator 444 are configured to communicate with each other using one or more of the following communication protocols such as Bluetooth®, ANT3®, KNX®, ZWave®, X10® Wireless USB®, IrDA®, Nanonet®, Tiny OS®, ZigBee®, 802.11 IEEE, and other radio, infrared, UHF, VHF communications and the like. In one embodiment, the transceiver 400 may be a radio frequency identification (RFID) tag either active or passive, depending on the interrogator capabilities of the transceiver 402.

FIG. 12 illustrates a control system 501 including the microcontroller 500 which is coupled to the position and speed calculators 416 and 422, the loading unit identification system 440, the user interface 120, the drive motor 200, and a data storage module 502. In addition the microcontroller 500 may be directly coupled to the motion sensor 251 and various other sensors (e.g., first and second tissue sensors 177 and 179, the load switch 230, shaft start position sensor 231, clamp position sensor 232, articulation sensor 235, linear displacement sensor 237, rotational sensor 239, firing rod rotation sensor 241, motor and battery operating module 412, rotation speed detecting apparatus 418, switches 421, voltage sensor 428, current sensor 430, and interrogator 444).

The microcontroller 500 includes internal memory which stores one or more software applications (e.g., firmware) for controlling the operation and functionality of the surgical instrument 10. The microcontroller 500 processes input data from the user interface 120 and adjusts the operation of the surgical instrument 10 in response to the inputs. The adjustments to the surgical instrument 10 may including powering the surgical instrument 10 on or off, speed control by means of voltage regulation or voltage pulse width modulation, torque limitation by reducing duty cycle or pulsing the voltage on and off to limit average current delivery during a predetermined period of time.

The microcontroller 500 is coupled to the user interface 120 via a user feedback module 504 which is configured to inform the user of operational parameters of the surgical instrument 10. The user feedback module 504 instructs the user interface 120 to output operational data on the screen 122. In particular, the outputs from the sensors are transmitted to the microcontroller 500 which then sends feedback to the user instructing the user to select a specific mode, speed or function for the surgical instrument 10 in response thereto.

The loading unit identification system 440 instructs the microcontroller 500 which end effector is on the loading unit. In an embodiment, the control system 501 is capable of storing information relating to the force applied to firing rod 220 and/or end effector 160, such that when the loading unit 169 is identified the microcontroller 500 automatically selects the operating parameters for the surgical instrument 10. This allows for control of the force being applied to the firing rod 220 so that firing rod 220 can drive the particular end effector 160 that is on the loading unit in use at the time.

The microcontroller 500 also analyzes the calculations from the position and speed calculators 416 and 422 and other sensors to determine the actual position, direction of motion, and/or speed of the firing rod 220 and operating status of components of the surgical instrument 10. The analysis may include interpretation of the sensed feedback signal from the calculators 416 and 422 to control the movement of the firing rod 220 and other components of the surgical instrument 10 in response to the sensed signal. The microcontroller 500 is configured to limit the travel of the firing rod 220 once the firing rod 220 has moved beyond a predetermined point as reported by the position calculator 416. Additional parameters which may be used by the microcontroller 500 to control the surgical instrument 10 include motor and/or battery temperature, number of cycles remaining and used, remaining battery life, tissue thickness, current status of the end effector, transmission and reception, and external device connection status.

In one embodiment, the surgical instrument 10 includes various sensors configured to measure current (e.g., an ammeter), voltage (e.g., a voltmeter), proximity (e.g., optical sensors), temperature (e.g., thermocouples and thermistors), and force (e.g., strain gauges and load cells) to determine for loading conditions on the loading unit 169. During operation of the surgical instrument 10 it is desirable to know the forces being exerted by the surgical instrument 10 on the target tissue during the approximation process and during the firing process. Detection of abnormal loads (e.g., outside a predetermined load range) indicates a problem with the surgical instrument 10 and/or clamped tissue which is communicated to the user.

Monitoring of load conditions may be performed by one or more of the following methods: monitoring speed of the drive motor 200, monitoring torque being applied by the drive motor 200, proximity of jaw members 162, 164, monitoring temperature of components of the surgical instrument 10, measuring the load on the firing rod 220 via a strain sensor 185 (FIG. 4) and/or other load bearing components of the surgical instrument 10. Speed and torque monitoring is discussed above with respect to FIG. 6 and the speed calculator 422.

In another embodiment, the firing rod 220 or other load-bearing components include one or more strain gauges and/or load sensors disposed thereon. Under high strain conditions, the pressure exerted on the surgical instrument 10 and/or the end effector 160 is translated to the firing rod 220 causing the firing rod 220 to deflect, leading to increased strain thereon. The strain gauges then report the stress measurements to the microcontroller 500. In another embodiment, a position, strain or force sensor may be disposed on the clutch plate 700.

During the approximation process, as the end effector 160 is clamped about tissue, the sensors disposed in the surgical instrument 10 and/or the end effector 160 indicate to the microcontroller 500 that the end effector 160 is deployed about abnormal tissue (e.g., low or high load conditions). Low load conditions are indicative of a small amount of tissue being grasped by the end effector 160 and high load conditions denote that too much tissue and/or a foreign object (e.g., tube, staple line, clips, etc.) is being grasped. The microcontroller 500 thereafter indicates to the user via the user interface 120 that a more appropriate loading unit 169 and/or instrument 10 should be chosen.

During the firing process, the sensors can alert the user of a variety of errors. Sensors may communicate to the microcontroller 500 that a staple cartridge or a portion of the surgical instrument 10 is faulty. In addition, the sensors can detect sudden spikes in the force exerted on the knife, which is indicative of encountering a foreign body. Monitoring of force spikes could also be used to detect the end of the firing stroke, such as when the firing rod 220 encounters the end of the stapling cartridge and runs into a hard stop. This hard stop creates a force spike which is relatively larger than those observed during normal operation of the surgical instrument 10 and could be used to indicate to the microcontroller that the firing rod 220 has reached the end of loading unit 169. Measuring of the force spikes can be combined with positional feedback measurements (e.g., from the motion sensor 251) as discussed with respect to position and speed calculators 416 and 422. This allows for use of various types of staple cartridges (e.g., multiple lengths) with the surgical instrument 10 without modifying the end effector 160.

When force spikes are encountered, the surgical instrument 10 notifies the user of the condition and enters a so-called "pulse" or an electronic clutching mode. During this mode the drive motor 200 is controlled to run only in short bursts to allow for the pressure between the grasped tissue and the end effector 160 to equalize. The electronic clutching limits the torque exerted by the drive motor 200 and avoids situations where high amounts of current are drawn from the power source 400. This, in turn, limits damage to electronic and mechanical components due to overheating that accompanies overloading and high-current draw situations.

The microcontroller 500 may control the drive motor 200 through a motor driver via a pulse width modulated control signal. The motor driver is configured to adjust the speed of the drive motor 200 either in clockwise or counter-clockwise direction. The motor driver is also configured to switch between a plurality of operational modes which include an electronic motor braking mode, a constant speed mode, an electronic clutching mode, and a controlled current activation mode. In electronic braking mode, two terminal of the drive motor 200 are shorted and the generated back EMF counteracts the rotation of the drive motor 200 allowing for faster stopping and greater positional precision in adjusting the linear position of the firing rod 220.

In the constant speed mode, the speed calculator 422 in conjunction with the microcontroller 500 and/or the motor driver adjust the rotational speed of the drive motor 200 to ensure constant linear speed of the firing rod 220. The electronic clutching mode involves repeated engagement and/or disengagement of the clutch 300 from the drive motor 200 in response to sensed feedback signals from the position and speed calculators 416 and 422. In controlled current activation mode, the current is either ramped up or down to limit damaging current and torque spikes when transitioning between static and dynamic mode to provide for so-called "soft start" and "soft stop."

The data storage module 502 records the data from the sensors coupled to the microcontroller 500. In addition, the data storage module 502 may record the identifying code of the loading unit 169, the status of the end effector 100, the number of stapling cycles during the procedure, and other information relating to the status of components of the surgical instrument 10. The data storage module 502 is also configured to connect to an external device such as a personal computer, a PDA, a smartphone, or a storage device (e.g., a Secure Digital™ card, a CompactFlash® card, or a Memory Stick™) through a wireless or wired data port 503. This allows the data storage module 502 to transmit performance data to the external device for subsequent analysis and/or storage. The data port 503 also allows for "in the field" upgrades of the firmware of the microcontroller 500.

Embodiments of the present disclosure may include a feedback control system 601 as shown in FIGS. 13-16. The system includes a feedback controller 603. The surgical instrument 10 is connected to the feedback controller 603 via the data port 502 which may be either wired (e.g., FireWire®, USB, Serial RS232, Serial RS485, USART, Ethernet, etc.) or wireless (e.g., Bluetooth®, ANT3®, KNX®, Z-Wave®, X10®, Wireless USB®, Wi-Fi®, IrDA®, nanoNET®, TinyOS®, ZigBee®, 802.11 IEEE, and other radio, infrared, UHF, VHF communications and the like).

Figure 13:
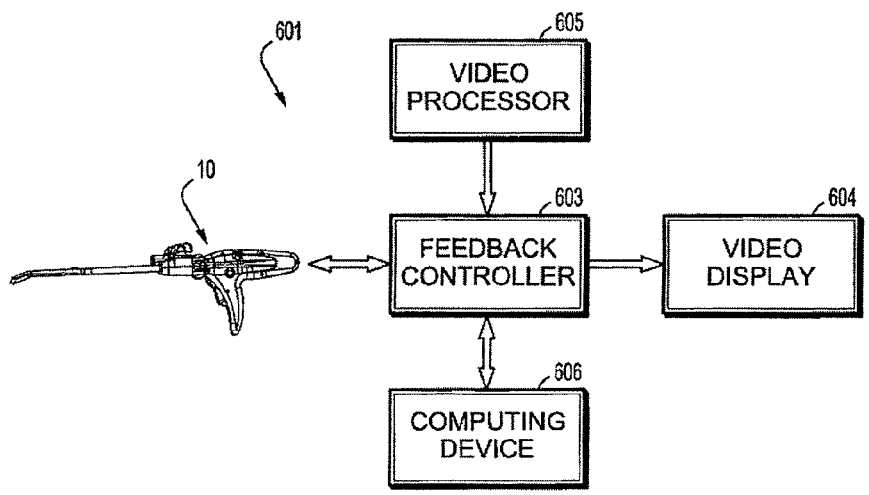
FIG. 13 is a schematic diagram of a feedback control system in accordance with an embodiment of the present disclosure.

With reference to FIG. 13, the feedback controller 603 is configured to store the data transmitted to it by the surgical instrument 10 as well as process and analyze the data. The feedback controller 603 is also connected to other devices, such as a video display 604, a video processor 605 and a computing device 606 (e.g., a personal computer, a PDA, a smartphone, a storage device, etc.). The video processor 605 is used for processing output data generated by the feedback controller 603 for output on the video display 604. The computing device 606 is used for additional processing of the feedback data. In one embodiment, the results of the sensor feedback analysis performed by the microcontroller 600 may be stored internally for later retrieval by the computing device 606.

The feedback controller 603 includes a data port 607 (FIG. 15) coupled to the microcontroller 600 which allows the feedback controller 603 to be connected to the computing device 606. The data port 607 may provide for wired and/or wireless communication with the computing device 606 providing for an interface between the computing device 606 and the feedback controller 603 for retrieval of stored feedback data, configuration of operating parameters of the feedback controller 603 and upgrade of firmware and/or other software of the feedback controller 603.

The feedback controller 603 is further illustrated in FIGS. 14-15. The feedback controller 603 includes a housing 610 and a plurality of input and output ports, such as a video input 614, a video output 616, a heads-up ("HUD") display output 618. The feedback controller 603 also includes a screen 620 for displaying status information concerning the feedback controller 603.

Components of the feedback controller 603 are shown in FIG. 16. The feedback controller 603 includes a microcontroller 600 and a data storage module 602. The microcontroller 600 and the data storage module 602 provide similar functionality as the microcontroller 500 and the data storage module 502 of the surgical instrument 10. Providing these components in a stand-alone module, in the form of the feedback controller 603, alleviates the need to have these components within the surgical instrument 10.

The data storage module 602 may include one or more internal and/or external storage devices, such as magnetic hard drives, flash memory (e.g., Secure Digital® card, Compact Flash® card, or MemoryStick®) The data storage module 602 is used by the feedback controller 603 to store feedback data from the surgical instrument 10 for later analysis of the data by the computing device 606. The feedback data may include information supplied by the motion sensor 251 and other sensors disposed within the surgical instrument 10.

The microcontroller 600 may supplant, complement, or supplement the control circuitry of the surgical instrument 10. The microcontroller 600 includes internal memory which stores one or more software applications (e.g., firmware) for controlling the operation and functionality of the surgical instrument 10. The microcontroller 600 processes input data from the user interface 120 and adjusts the operation of the surgical instrument 10 in response to the inputs. The microcontroller 600 is coupled to the user interface 120 via a user feedback module 504 which is configured to inform the user of operational parameters of the surgical instrument 10. More specifically, the surgical instrument 10 is configured to connect to the feedback controller 603 wirelessly or through a wired connection via a data port 407 (FIG. 6).

In a disclosed embodiment, the microcontroller 600 is connected to the drive motor 200 and is configured and arranged to monitor the battery impedance, voltage, temperature and/or current draw and to control the operation of the surgical instrument 10. The load or loads on battery 400, transmission, drive motor 200 and drive components of the surgical instrument 10 are determined to control a motor speed if the load or loads indicate a damaging limitation is reached or approached. For example, the energy remaining in battery 400, the number of firings remaining, whether battery 400 must be replaced or charged, and/or approaching the potential loading limits of the surgical instrument 10 may be determined. The microcontroller 600 may also be connected to one or more of the sensors of the surgical instrument 10 discussed above, including the motion sensor 251 (FIG. 6).

The microcontroller 600 is also configured to control the operation of drive motor 200 in response to the monitored information. Pulse modulation control schemes, which may include an electronic clutch, may be used in controlling the surgical instrument 10. For example, the microcontroller 600 can regulate the voltage supply of the drive motor 200 or supply a pulse modulated signal thereto to adjust the power and/or torque output to limit system damage or optimize energy usage.

In one embodiment, an electric braking circuit may be used for controlling drive motor 200, which uses the existing back electromotive force of rotating drive motor 200 to counteract and substantially reduce the momentum of drive tube 210. The electric braking circuit may improve the control of drive motor 200 and/or drive tube 210 for stopping accuracy and/or shift location of powered surgical instrument 10. Sensors for monitoring components of the powered surgical instrument 10 to help inhibit overloading of the powered surgical instrument 10 may include thermal-type sensors, such as thermal sensors, thermistors, thermopiles, thermo-couples and/or thermal infrared imaging and provide feedback to the microcontroller 600. The microcontroller 600 may control the components of powered surgical instrument 10 in the event that limits are reached or approached and such control can include cutting off the power from the power source 400, temporarily interrupting the power or going into a pause mode and/or pulse modulation to limit the energy used. The microcontroller 600 can also monitor the temperature of components to determine when operation can be resumed. The above uses of the microcontroller 600 may be used independently of or factored with current, voltage, temperature and/or impedance measurements.

The result of the analysis and processing of the data by the microcontroller 600 is output on video display 604 and/or the HUD display 622. The video display 604 may be any type of display such as an LCD screen, a plasma screen, electroluminescent screen and the like. In one embodiment, the video display 604 may include a touch screen and may incorporate resistive, surface wave, capacitive, infrared, strain gauge, optical, dispersive signal or acoustic pulse recognition touch screen technologies. The touch screen may be used to allow the user to provide input while viewing operational feedback. The HUD display 622 may be projected onto any surface visible to the user during surgical procedures, such as lenses of a pair of glasses and/or goggles, a face shield, and the like. This allows the user to visualize vital feedback information from the feedback controller 603 without loosing focus on the procedure.

The feedback controller 603 includes an on-screen display module 624 and a HUD module 626. The modules 626 process the output of the microcontroller 600 for display on the respective displays 604 and 622. More specifically, the OSD module 624 overlays text and/or graphical information from the feedback controller 603 over other video images received from the surgical site via cameras disposed therein. The modified video signal having overlaid text is transmitted to the video display 604 allowing the user to visualize useful feedback information from the surgical instrument 10 and/or feedback controller 603 while still observing the surgical site.

Figure 17:
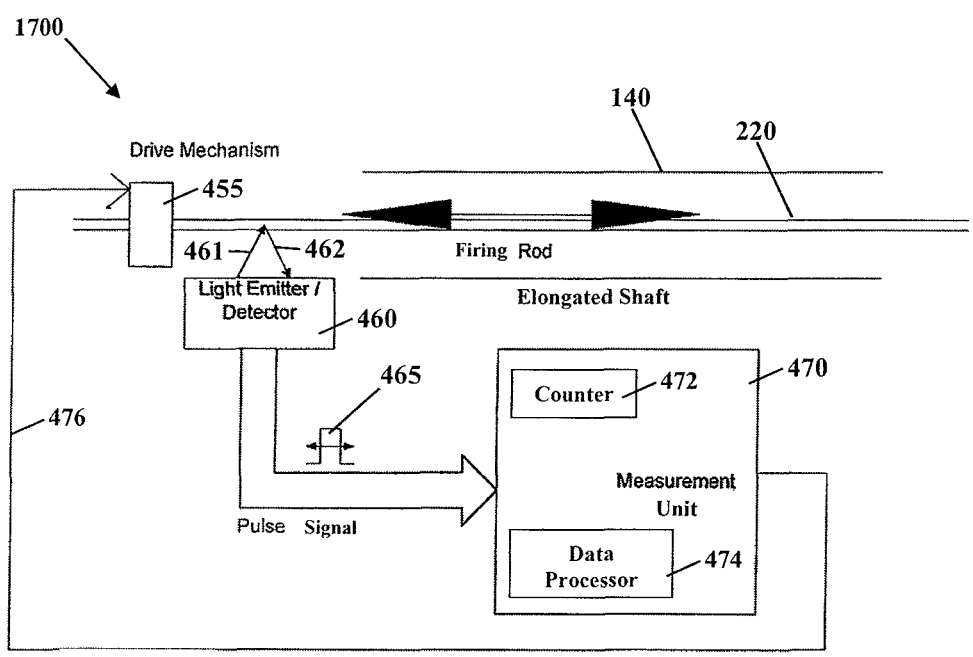
FIG. 17 is a block diagram of a feedback control system for controlling the motion of a firing rod in accordance with an embodiment of the present disclosure.

FIG. 17 is a block diagram of a feedback control system 1700 for controlling parameters of the motion of the firing rod 220, including the position and velocity of the firing rod 220, according to some embodiments. Components of the feedback control system 1700 may be implemented in the control system 501 of FIG. 12 or the feedback controller 603 of FIG. 16. The feedback control system 1700 includes the motion sensor 251, which, in some embodiments, includes a light emitter and detector unit 460, a measurement unit 470, and the microcontroller 500. The light emitter and detector unit 460 may include a laser diode for emitting light and a light sensitive transistor for detecting reflected light. In other embodiments, the light emitter and detector unit 460 is replaced with a light emitter and detector unit that emits light in the electromagnetic spectrum. The light emitter and detector unit 460 focuses a light beam 461 on the surface of the firing rod 220 and detects light 462 reflected from the surface of the firing rod 220. The light emitter and detector unit 460 generates a pulse signal 465 with a frequency or pulse width that varies with motion of scribes or other markings 464 (see FIG. 18) transverse to the direction of motion of the surface of the firing rod 220.

The motion sensor 251 transmits the pulse signal 465 to the measurement unit 470 via a wired or wireless communications channel. For example, the motion sensor 251, in some embodiments, may be physically attached to the firing rod 220 and the motion sensor 251 may include wireless communications circuitry configured to transmit the pulse signal 465 to the measurement unit 470 via a wireless communications link.

The measurement unit 470 includes a counter 472 and a data processor 474. The counter 472 counts pulses in the pulse signal 465 and the data processor 474 computes the frequency of the pulse signal 465 based on the rate of the counted pulses. The count and or the computed frequency is then used to determine the position and velocity of the firing rod 220. Alternatively, in other embodiments, the measurement unit 470 may include circuitry for determining the width of the pulses in the pulse signal 465. The measured pulse width of the pulse signal 465 may then be used to determine a parameter of the motion of the firing rod 220 such as an end or intermediate point in the stroke. For instance, the length and or distances between markings 464 may be varied to indicated special conditions, such as the end point of a stroke.

The data processor 474 may determine a number of parameters of the motion of the firing rod 220 based on the count, frequency or pulse width of the pulse signal 465. For example, the data processor 474 (or the position calculator 416 of FIG. 12) may determine the position at which a force is applied to the firing rod 220. The data processor 474 may also determine the distance that the firing rod 220 moves during a predetermined time period. The data processor 474 may also determine the direction of motion of the firing rod 220 (i.e., the data processor 474 may determine whether the firing rod 220 is being inserted into the elongated shaft 140 or is being retracted out of the elongated shaft 140). The data processor 474 (or the speed calculator 422 of FIG. 12) may also determine the velocity of the firing rod 220.

In one embodiment, the light emitter and detector unit 460 generates a pulse signal 465 with a light frequency that varies with a change in a parameter of the light 462 reflected from the surface of the firing rod 220. For example, at a first position of the firing rod 220, the light emitter and detector unit 460 may generate a pulse signal 465 with a first frequency when it detects light with a first wavelength reflected from the bare surface 466 of the firing rod 220. At a second position, the light emitter and detector unit 460 may generate a pulse signal 465 with a second light frequency when it detects light with a second different wavelength reflected from a reflective marking on the firing rod 220. The pulse signal 465 information can then be used to determine the motion of the firing rod 220 from a first position to a second position. In some embodiments, the light emitter and detector unit 460 may sense a change in other parameters of the light 462 reflected from the firing rod 220, including the intensity, polarization, or phase of the light 462, and generate a corresponding change in the frequency or pulse width of the pulse signal 465 from which a parameter of the motion of the firing rod 220 (e.g., the velocity of the firing rod 220) can be computed. In other embodiments, the light emitter 460 may emit different frequencies of light to generate different reflected light frequencies created by using markings 464 having different reflected light responses to the emitted frequencies.

Figure 18A:
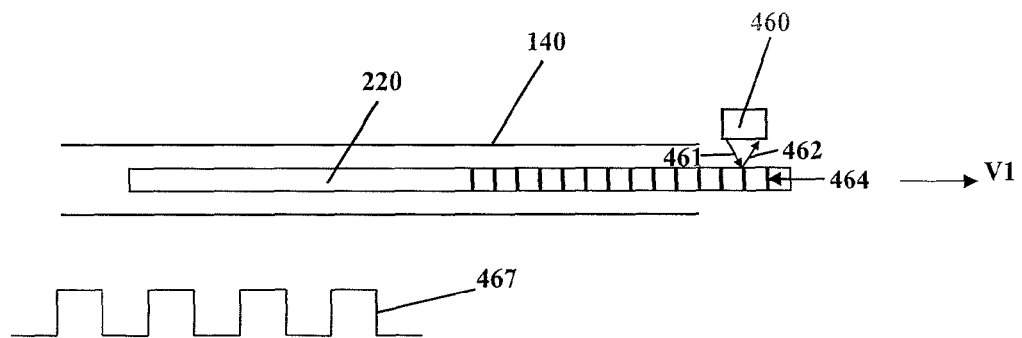
FIGS. 18A and 18B are diagrams illustrating how a pulse signal output from a light emitter and detector unit responds to a change in the light reflected from the surface of the firing rod that results from the motion of the firing rod with respect to the elongated shaft in accordance with an embodiment of the present disclosure.
Figure 18B:
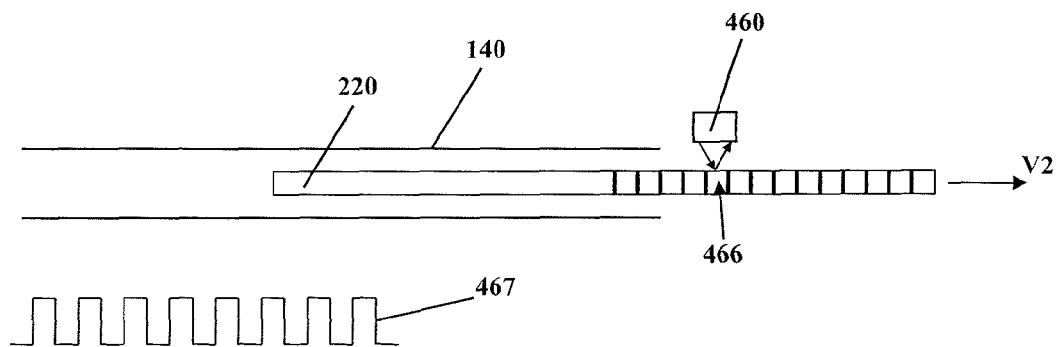

FIGS. 18A and 18B are diagrams that illustrate how the pulse signal 465 output from the light emitter and detector unit 460 responds to changes in a parameter of the light reflected from the surface of the firing rod 220 with respect to the elongated shaft 140. In this embodiment, the light emitter and detector unit 460 is fixed with respect to the elongated shaft 140. The firing rod 220 includes a series of markings 464 that can be detected by the light emitter and detector unit 460. In some embodiments, the markings 464 are detected by analyzing the parameters of the light reflected from the markings 464. The markings 464 are separated a predetermined distance by the bare surface 466 of the firing rod 220. For example, the markings 464 may be spaced 1 to 5 mm apart. In some embodiments, the markings 464 include a material with reflective properties that are different from the reflective properties of the bare surface 466 of the firing rod 220. In other embodiments, the markings 464 may be separated by a second material that coats the surface of the firing rod 220. The second material has reflective properties that are different from the reflective properties of the markings 464. The differences between the reflective properties of the materials may be configured to improve or optimize the detection of the markings 464.

As illustrated in FIG. 18A, the firing rod 220 is disposed within the elongated shaft 140 at a first position. In this first position, the emitter and detector unit 460 emits a light beam 461 on one of the multiple markings 464 on the firing rod 220 moving at a first velocity V1. The emitter and detector unit 460 then detects a parameter of the reflected light beam (e.g., the count, duration or wavelength of the light beam) that corresponds to the reflective properties of the marking 464. Upon detecting the parameter of the reflected light beam, the emitter and detector unit 460 generates a first pulse signal 467 with a first count, a first pulse width or a first frequency. From these parameters the position and velocity of the firing rod 220 may be determined.

As shown in FIG. 18B, when the firing rod 220 moves in a proximal direction out of the elongated shaft 140 to a second position and at a second velocity V2, the light emitter and detector unit 460 may emit a light beam on the bare surface 466 of the firing rod 220 or a material (that is different from the material of the markings 464) that coats the bare surface 466 of the firing rod 220. In this case, the emitter and detector unit 460 generates a second pulse signal 468 with a higher pulse frequency than the first pulse signal 467 in FIG. 18A due to the relatively higher velocity. In other words, the emitter and detector unit 460 generates the second pulse signal 468 that includes pulses having a narrower pulse width than the pulses in the first pulse signal 467. Thus, as the firing rod 220 moves, the light emitter and detector unit 460 detects multiple transitions from the markings 464 to the bare surface 466 of the firing rod 466 and generates shorter duration second pulse signals 468. The counter 472 of FIG. 17 may count the second pulse signals 468. Then, the data processor 474 of FIG. 17 may compute a change in position of the firing rod 220 based on the number of transitions counted. For example, if the counter 472 counts three second pulse signals 468 and assuming that the markings 464 on the firing are 1 mm apart, then the data processor 474 computes a change in position of 3 mm (i.e., 3 transitions×1 mm between markings 464).

In some embodiments, the measurement unit 470 computes a position and/or velocity of the firing rod 220 based on the light reflected from the surface of a firing rod and provides the position and/or velocity information to the microcontroller 500. The microcontroller 500 executes a control algorithm (e.g., a proportional control algorithm or a proportional-integral-derivative (PID) control algorithm), which uses the computed position and/or velocity of the firing rod 220, to generate a voltage command. The voltage command is fed back 476 to a powered-drive mechanism 455 (e.g., the rotary motor 200) to form a closed-loop feedback system. In this configuration, the position and/or velocity of the firing rod 220 can be accurately controlled.

Figure 19:
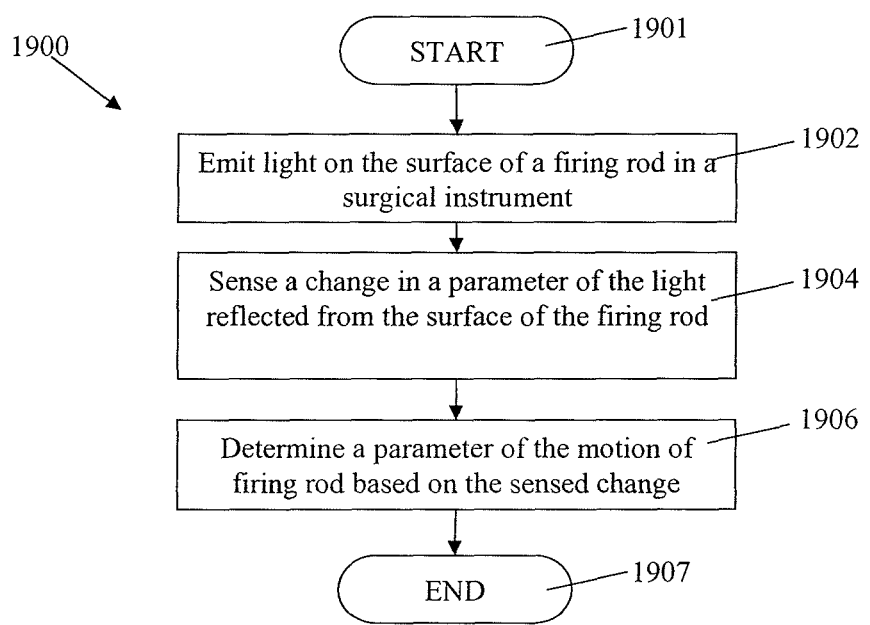
FIG. 19 is a flow diagram of a process for determining a parameter of the motion of a firing rod in a surgical instrument in accordance with an embodiment of the present disclosure.

FIG. 19 is a flow diagram of a process 1900 for determining a parameter of the motion of a firing rod in a surgical instrument according to an embodiment. After the process 1900 starts 1901, light is emitted on the surface of a firing rod in a surgical instrument 1902. In various embodiments, the light may include infrared radiation, visible light or ultraviolet radiation. Next, changes in a parameter of the light reflected from the surface of the firing rod are sensed 1904. Before the process 1900 ends 1907, a parameter of the motion of the firing rod is determined based on the sensed changes 1906.

Figure 20:
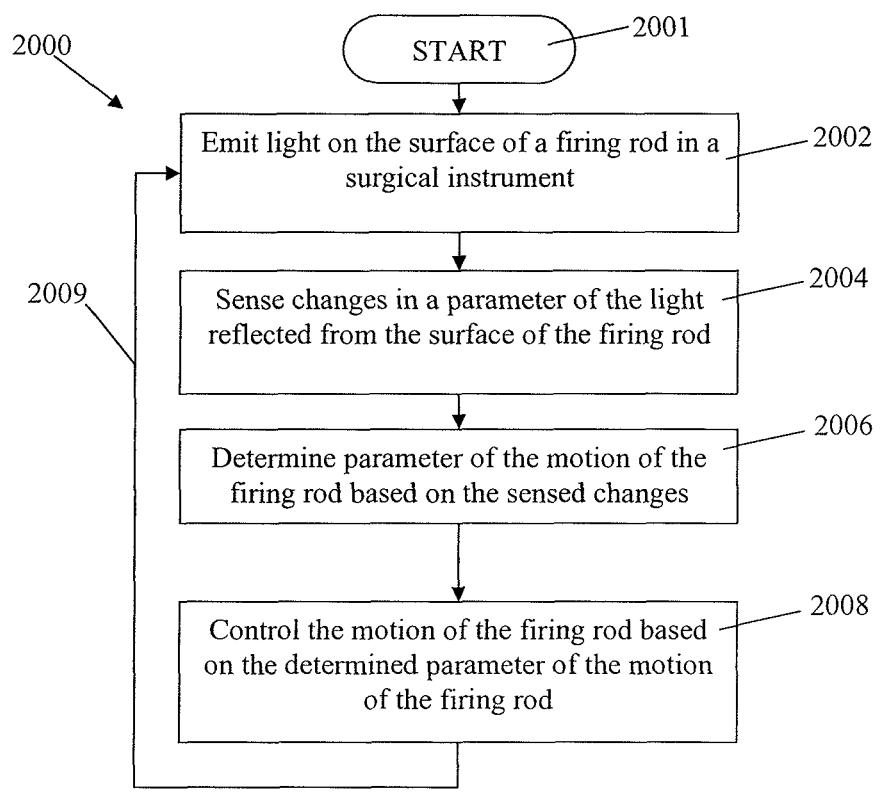
FIG. 20 is a flow diagram of a process for operating a surgical instrument in accordance with an embodiment of the present disclosure.

FIG. 20 is a flow diagram of a process 2000 for operating a surgical instrument according to another embodiment. After the process 2000 starts 2001, light is emitted on the surface of a firing rod in a surgical instrument 2002. Then, changes in a parameter of the light reflected from the surface of the firing rod are sensed 2004. Next, a parameter of the motion of the firing rod is determined based on the sensed changes in a parameter of the reflected light 2006. Then, before the process 2000 returns 2009 to step 2002 to emit light on the surface of the firing rod, the motion of the firing rod is controlled (e.g., through a driving mechanism that physically moves the firing rod) based on the determined parameter of the motion of the firing rod 2008.

Figure 21:
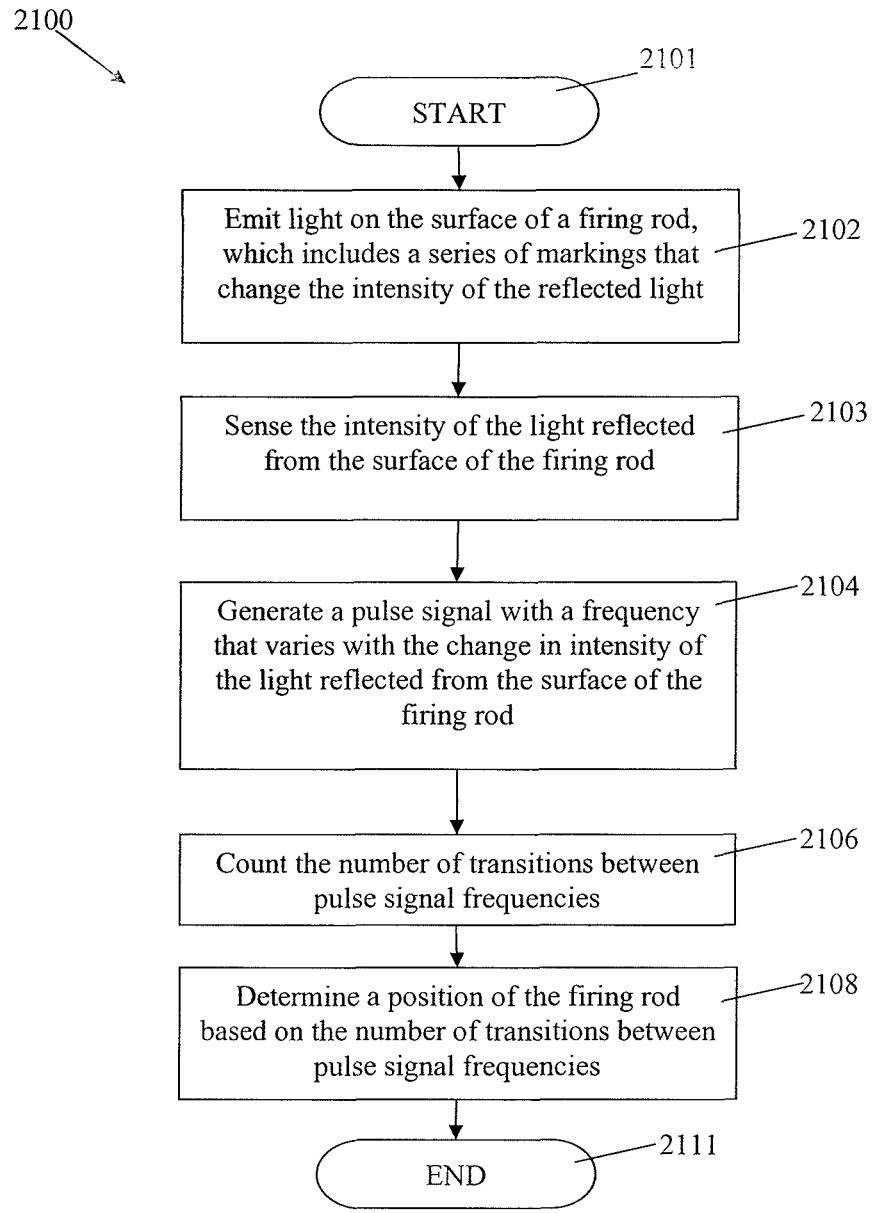
FIGS. 21 and 22 are flow diagrams of processes for determining parameters of the motion of a firing rod in a surgical instrument in accordance with embodiments of the present disclosure.

FIG. 21 is a flow diagram of a process 2100 for determining a parameter of the motion of a firing rod in a surgical instrument according to another embodiment. After the process 2100 starts 2101, light is emitted on the surface of a firing rod, which includes a series of markings that change the intensity of the reflected light 2102. Then, the intensity of the light reflected from the surface of the firing rod is sensed 2103. A pulse signal is generated with a frequency (or a pulse width) that varies with the change in intensity of the light reflected from the surface of the firing rod 2104 and the number of transitions between pulse signal frequencies is counted 2106. Then, before the process 2100 ends 2111, the position of the firing rod is determined based on the number of transitions between pulse signal frequencies 2108 (or the pulse width of pulse signals).

Figure 22:
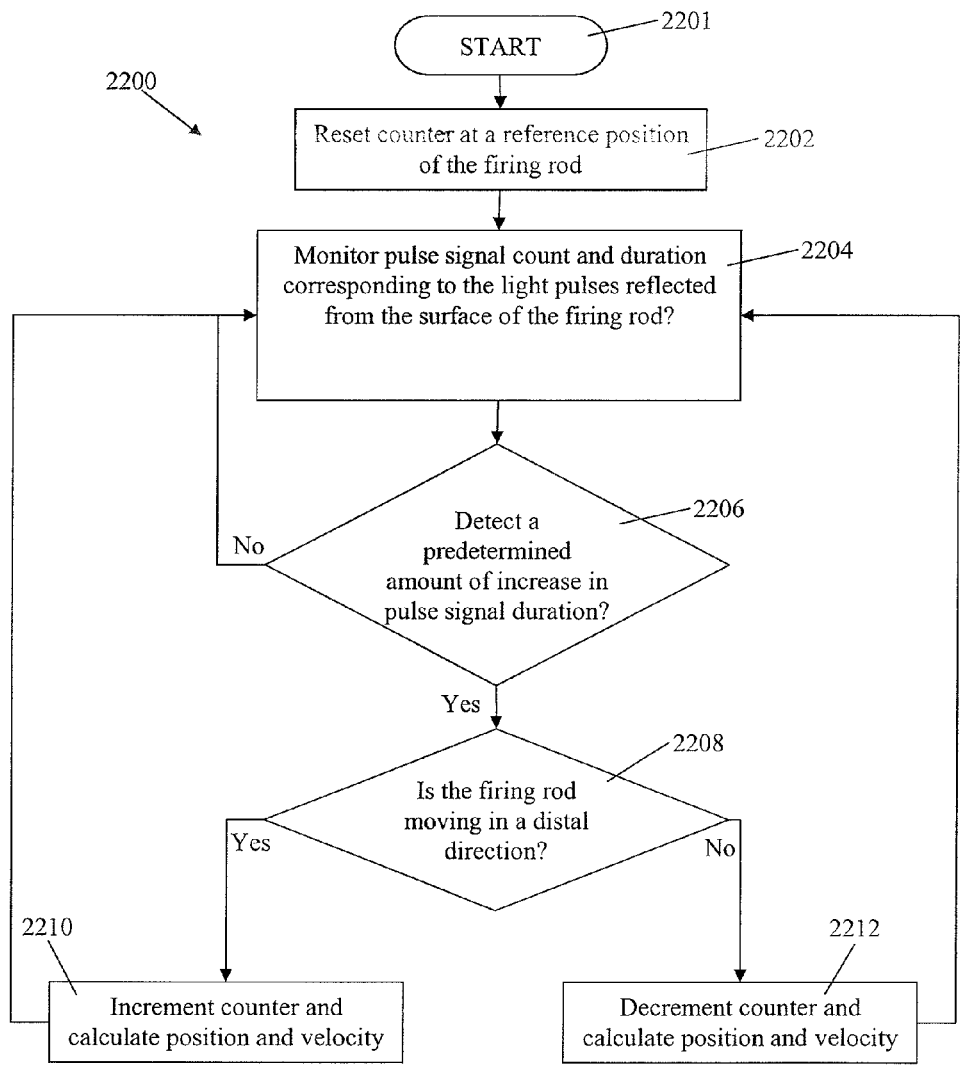

FIG. 22 is a flow diagram of a process 2200 for determining parameters of the motion of a firing rod in a surgical instrument according to another embodiment. After the process 2200 starts 2201, a counter (e.g., the counter 472 of FIG. 17) is reset 2202 at a reference position of the firing rod (e.g., at the position where the firing rod is fully retracted). After the counter is reset, the pulse count and duration of a pulse signal (e.g., the pulse signal 465 generated by the light emitter and detector unit 460) is monitored 2204.

If the light emitter and detector unit detects a predetermined amount of increase in the pulse signal duration 2206 (e.g., the pulse width of the pulse signal doubles in size) and the firing rod is moving in the distal direction 2208, then the counter (e.g., the counter 472 of FIG. 17) is incremented and the position and velocity of the firing rod are calculated 2210. For example, in some embodiments, the distance between markings on the firing rod may be 1 mm. If the counter had been incremented ten times (corresponding to the detection of ten markings on the firing rod) in one second, then the position of the firing rod is 10 mm (1 cm) relative to the reference position of the firing rod (at the time the counter was reset) and the velocity is 0.01 m/s. In some instances, certain of the marking are placed at greater intervals to provide indications of end points or the direction of travel of the firing rod.

On the other hand, if the light emitter and detector unit detects a predetermined amount of increase in the pulse signal duration 2206 and the firing rod is not moving in the distal direction 2208, but is moving in the proximal direction, then the counter is decremented and the position and velocity of the firing rod are calculated 2212. For example, in some embodiments, the distance between markings on the firing rod may be 1 mm. If the counter had been incremented ten times (corresponding to the detection of ten markings on the firing rod while it was moving in the distal direction) and decremented five times (corresponding to the detection of five markings on the firing rod while it was moving in the proximal direction), then the position of the firing rod is 5 mm relative to the reference position of the firing rod (i.e., 10 mm in the distal direction–(minus) 5 mm in the proximal direction=5 mm relative to the reference position).

After incrementing or decrementing the counter and calculating the position and velocity of the firing rod 2210, 2212, the process 2200 continues to monitor 2204 the pulse duration of the pulse signal generated by the light emitter and detector unit.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A surgical instrument, comprising:
   a housing;
   an elongated shaft extending distally from the housing and defining a first longitudinal axis;
   a firing rod disposed within the elongated shaft, the firing rod having a plurality of markings that vary reflective properties of a surface of the firing rod;
   a drive mechanism disposed at least partially within the housing, the drive mechanism in mechanical cooperation with the firing rod;
   a sensor that senses a parameter of light reflected from the surface of the firing rod, the sensor having a light emitter and detector unit that generates and emits light on the surface of the firing rod; and
   a measurement unit that determines a parameter of motion of the firing rod based on the sensed parameter of the light reflected from the surface of the firing rod.

2. The surgical instrument according to claim 1, wherein the light emitter and detector unit generates a pulse signal with a parameter that varies with a change in the sensed parameter of the light reflected from the surface of the firing rod, and the measurement unit determines the parameter of motion of the firing rod based on the change in the parameter of the pulse signal.

3. The surgical instrument according to claim 2, wherein the parameter of the pulse signal is a frequency of the pulse signal.

4. The surgical instrument according to claim 2, wherein the parameter of the pulse signal is a pulse duration of the pulse signal.

5. The surgical instrument according to claim 1, wherein the measurement unit includes a counter that counts a number of markings of the plurality of markings that are exposed to the light emitted from the light emitter and detector unit based on a change in the sensed parameter of the light reflected from the surface of the firing rod.

6. The surgical instrument according to claim 1, wherein the parameter of motion of the firing rod is a position of the firing rod.

7. The surgical instrument according to claim 1, wherein the parameter of motion of the firing rod is a velocity of the firing rod.

8. The method according to claim 1, wherein the sensed parameter of the light is phase, frequency, intensity, or polarization.

9. The surgical instrument according to claim 1, further comprising:
   a control unit that controls the drive mechanism based on the parameter of motion of the firing rod determined by the measurement unit.

10. A method of determining a parameter of motion of a firing rod in a surgical instrument, comprising:
- emitting light on a surface of the firing rod in the surgical instrument wherein the surface of the firing rod comprises a plurality of markings that vary reflective properties of the surface of the firing rod;
- sensing a change in a parameter of the light reflected from the surface of the firing rod; and
- determining the parameter of motion of the firing rod based on the sensed change in the parameter of the light reflected from the surface of the firing rod.

11. A method of operating a surgical instrument, comprising:
- emitting light on a surface of a firing rod in the surgical instrument, wherein the surface of the firing rod comprises a plurality of markings that vary reflective properties of the surface of the firing rod;
- sensing a change in a parameter of the light reflected from the surface of the firing rod, comprising counting a number of markings of the plurality of markings on the firing rod that reflect the light;
- determining a parameter of motion of the firing rod based on the sensed change in the parameter of the light reflected from the surface of the firing rod; and
- controlling the motion of the firing rod based on the determined parameter of motion of the firing rod.

12. The method according to claim 11, wherein sensing a change in a parameter of the light reflected from the surface of the firing rod comprises generating a pulse signal with a parameter that varies with the change in the parameter of the light reflected from the surface of the firing rod, and wherein determining the parameter of motion of the firing rod comprises determining the parameter of motion of the firing rod based on the change in the parameter of the pulse signal.

13. The method according to claim 11, wherein the parameter of motion of the firing rod is the position of the firing rod.

14. The method according to claim 11, wherein the parameter of motion of the firing rod is the velocity of the firing rod.

15. The method according to claim 11, wherein the parameter of the light is phase, frequency, intensity, or polarization.

* * * * *